(12) United States Patent
Chen

(10) Patent No.: US 11,124,572 B2
(45) Date of Patent: Sep. 21, 2021

(54) HUMANIZED ANTI-PD-L1 ANTIBODIES

(71) Applicant: QLSF Biotherapeutics Inc., South San Francisco, CA (US)

(72) Inventor: Shihao Chen, San Mateo, CA (US)

(73) Assignee: QLSF BIOTHERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 16/852,313

(22) Filed: Apr. 17, 2020

(65) Prior Publication Data

US 2020/0332010 A1    Oct. 22, 2020

Related U.S. Application Data

(60) Provisional application No. 62/835,764, filed on Apr. 18, 2019.

(51) Int. Cl.
*C07K 16/28* (2006.01)

(52) U.S. Cl.
CPC ...... *C07K 16/2827* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen | C07K 16/2866 435/69.6 |
| 8,217,149 B2 * | 7/2012 | Irving | A61P 31/00 530/387.1 |
| 2017/0218066 A1 | 8/2017 | Zhou | |
| 2018/0066058 A1 | 3/2018 | Sainson et al. | |
| 2018/0169232 A1 | 6/2018 | Andrews et al. | |
| 2019/0016814 A1 | 1/2019 | Humphrey et al. | |
| 2019/0106494 A1 | 4/2019 | Wang et al. | |

OTHER PUBLICATIONS

Colman, Peter M. "Effects of amino acid sequence changes on antibody-antigen interactions." Research in Immunology 145.1 (1994): 33-36. (Year: 1994).*
Lubert Stryer, Biochemistry, 4th, WH Freeman, New York (1995) ISBN: 0-7167-2009-4 (Year: 1995).*
Janeway, Charles A. "Immunobiology: The Immune System in Health and Disease." 2005 (Year: 2005).*
Sela-Culang, Inbal, Vered Kunik, and Yanay Ofran. "The structural basis of antibody-antigen recognition." Frontiers in immunology 4 (2013): 302 (Year: 2013).*
D'Angelo, Sara, et al. "Many routes to an antibody heavy-chain CDR3: necessary, yet insufficient, for specific binding." Frontiers in immunology 9 (2018): 395. (Year: 2018).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
International Search Report on PCT/US2020/028862, dated Aug. 24, 2020.

* cited by examiner

*Primary Examiner* — Michael Szperka
*Assistant Examiner* — Lia E Taylor
(74) *Attorney, Agent, or Firm* — Lin Sun-Hoffman; Yong Chen; Liu Chen & Hoffman LLP

(57) ABSTRACT

The present disclosure provides isolated binding molecules that bind to and blocks PD-L1, vectors comprising a nucleic acid molecules encoding an amino acid sequence of the binding molecules, host cells containing the vectors, methods of making the binding molecules, pharmaceutical compositions containing the binding molecules, and methods of using such antibodies, antibody fragments and derivatives and polypeptides, including methods of treating a disease requiring stimulation of immune responses including cancer.

18 Claims, 3 Drawing Sheets

Specification includes a Sequence Listing.

HUMANIZED ANTI-PD-L1 ANTIBODIES

CROSS REFERENCE TO RELATED APPLICATION

This application claims priority to U.S. Provisional Application No. 62/835,764, filed Apr. 18, 2019, the disclosure of which is incorporate herein by reference in its entirety.

INCORPORATION OF SEQUENCE LISTING

This application includes a Sequence Listing which is being submitted in ASCII format via EFS-Web, named "QLSF003US_ST25.txt," which is 158 KB in size and created on Apr. 17, 2020. The contents of the Sequence Listing are incorporated herein by reference in their entirety.

BACKGROUND OF THE INVENTION

Programmed cell death protein 1 (PD-1) is a 288 amino acid cell surface protein molecule and is encoded by the PDCD1 gene in humans. PD-1 is a type I trans-membrane protein containing an immunoglobulin-variable-type-amino-terminal-extracellular domain, a transmembrane region, and a cytoplasmic tail with an immunoreceptor tyrosine-based inhibitory motif and an immunoreceptor tyrosine-based switch motif (Ishida et al., 1992). PD-1 is expressed in pro-B cells and activated T cells, but not on resting T cells in vivo. Programmed death-1 (PD-1) acts as a checkpoint protein on immune cells. It negatively regulates the immune system through inhibition of effective T cell function by engaging PD-L1, a ligand for the PD-1 receptor.

The PD-1/PD-L1 interaction plays an important role in autoimmunity as well as in cancer immunology. PD-L1 expression has been observed in a variety of cancers including melanoma and non-small cell lung cancer. Many studies suggest that cancer cells overexpress PD-L1, which helps them evade immune attack by using the PD-1/PD-ligand (PDL) pathway. Based on the conclusion of these studies, several checkpoint blockade inhibitors for PD-1/PDL pathway were developed.

PD-1/PD-L1 blockade has achieved great clinical success in combating cancers. Several immune-therapies, such as Pembrolizumab (Keytruda) and Nivolumab (Opdivo), which target PD-1 and Atezolizumab (Tecentriq), Avelumab (Bavencio) and Durvalumab (Imfinzi) which target PD-L1, are effective in blocking the binding between PD-1 and PD-L1 which can reverse T cell dysfunction. However, in many advanced cancers, the objective response rate with monotherapy is only 20% (Xu-Monette et al., 2017).

As a result, improved therapeutics targeting PD-1 and PD-L1 are an area of intense interest. Also, many other immunotherapies are now being tested in clinical trials as well, both alone and in combinations. Accordingly, there remains a need for more effective immunotherapy targeting PD-1/PD-L1 pathway either used alone or in combination with other therapeutic agents in drug treatment regimens.

SUMMARY OF THE INVENTION

The present disclosure provides isolated monoclonal anti-PD-L1 antagonist antibodies, and antigen-binding portions thereof that specifically bind to human PD-L1.

In an aspect of the invention, an isolated monoclonal anti-PD-L1 antagonist antibody, or antigen-binding portion thereof comprises a heavy chain variable region CDR3 comprising SEQ ID NO:43. In some embodiments, the monoclonal anti-PD-L1 antagonist antibody, or antigen-binding portion thereof further comprises a heavy chain variable region CDR1 comprising SEQ ID NO:31 and a heavy chain variable region CDR2 comprising SEQ ID NO:37. In preferred embodiments, the monoclonal anti-PD-L1 antagonist antibody, or antigen-binding portion thereof further comprises: (a) a light chain variable region CDR1 comprising SEQ ID NO:13; (b) a light chain variable region CDR2 comprising SEQ ID NO:19; and (c) a light chain variable region CDR3 comprising SEQ ID NO:25.

In one embodiment, the antibody or portion comprises a light chain variable region amino acid sequence having at least 95% identity to SEQ ID NO:1 and a heavy chain variable region amino acid sequence having at least 95% identity to SEQ ID NO:7. In another embodiment, the antibody or portion comprises a heavy chain variable region comprising an amino acid sequence that has at least 95%, at least 96%, at least 97%, at least 98%, or at least 99% identical to a sequence as set forth in SEQ ID NO:7.

In another aspect of the invention, an isolated monoclonal anti-PD-L1 antagonist antibody, or antigen-binding portion thereof comprises a heavy chain variable region CDR3 comprising SEQ ID NO:44. In some embodiments, the monoclonal anti-PD-L1 antagonist antibody, or antigen-binding portion thereof further comprises a heavy chain variable region CDR1 comprising SEQ ID NO:32 and a heavy chain variable region CDR2 comprising SEQ ID NO:38. In preferred embodiments, the monoclonal anti-PD-L1 antagonist antibody, or antigen-binding portion thereof further comprises: (a) a light chain variable region CDR1 comprising SEQ ID NO:14; (b) a light chain variable region CDR2 comprising SEQ ID NO:20; and (c) a light chain variable region CDR3 comprising SEQ ID NO:26.

In one embodiment, the antibody or portion comprises a light chain variable region amino acid sequence having at least 95% identity to SEQ ID NO:2 and a heavy chain variable region amino acid sequence having at least 95% identity to SEQ ID NO:8. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:8.

In another aspect of the invention, an isolated monoclonal anti-PD-L1 antagonist antibody, or antigen-binding portion thereof comprises a heavy chain variable region CDR3 comprising SEQ ID NO:45. In some embodiments, the monoclonal anti-PD-L1 antagonist antibody, or antigen-binding portion thereof further comprises a heavy chain variable region CDR1 comprising SEQ ID NO:33 and a heavy chain variable region CDR2 comprising SEQ ID NO:39. In preferred embodiments, the monoclonal anti-PD-L1 antagonist antibody, or antigen-binding portion thereof further comprises: (a) a light chain variable region CDR1 comprising SEQ ID NO:15; (b) a light chain variable region CDR2 comprising SEQ ID NO:21; and (c) a light chain variable region CDR3 comprising SEQ ID NO:27.

In one embodiment, the antibody or portion comprises a light chain variable region amino acid sequence having at least 95% identity to SEQ ID NO:3 and a heavy chain variable region amino acid sequence having at least 95% identity to SEQ ID NO:9. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:9.

In another aspect of the invention, an isolated monoclonal anti-PD-L1 antagonist antibody, or antigen-binding portion thereof comprises a heavy chain variable region CDR3 comprising SEQ ID NO:46. In some embodiments, the monoclonal anti-PD-L1 antagonist antibody, or antigen-binding portion thereof further comprises a heavy chain variable region CDR1 comprising SEQ ID NO:34 and a heavy chain variable region CDR2 comprising SEQ ID NO:40. In preferred embodiments, the monoclonal anti-PD-L1 antagonist antibody, or antigen-binding portion thereof further comprises: (a) a light chain variable region CDR1 comprising SEQ ID NO:16; (b) a light chain variable region CDR2 comprising SEQ ID NO:22; and (c) a light chain variable region CDR3 comprising SEQ ID NO:28.

In one embodiment, the antibody or portion comprises a light chain variable region amino acid sequence having at least 95% identity to SEQ ID NO:4 and a heavy chain variable region amino acid sequence having at least 95% identity to SEQ ID NO:10. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:10.

In another aspect of the invention, an isolated monoclonal anti-PD-L1 antagonist antibody, or antigen-binding portion thereof comprises a heavy chain variable region CDR3 comprising SEQ ID NO:47. In some embodiments, the monoclonal anti-PD-L1 antagonist antibody, or antigen-binding portion thereof further comprises a heavy chain variable region CDR1 comprising SEQ ID NO:35 and a heavy chain variable region CDR2 comprising SEQ ID NO:41. In preferred embodiments, the monoclonal anti-PD-L1 antagonist antibody, or antigen-binding portion thereof further comprises: (a) a light chain variable region CDR1 comprising SEQ ID NO:17; (b) a light chain variable region CDR2 comprising SEQ ID NO:23; and (c) a light chain variable region CDR3 comprising SEQ ID NO:29.

In one embodiment, the antibody or portion comprises a light chain variable region amino acid sequence having at least 95% identity to SEQ ID NO:5 and a heavy chain variable region amino acid sequence having at least 95% identity to SEQ ID NO:11. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:11.

In another aspect of the invention, an isolated monoclonal anti-PD-L1 antagonist antibody, or antigen-binding portion thereof comprises a heavy chain variable region CDR3 comprising SEQ ID NO:48. In some embodiments, the monoclonal anti-PD-L1 antagonist antibody, or antigen-binding portion thereof further comprises a heavy chain variable region CDR1 comprising SEQ ID NO:36 and a heavy chain variable region CDR2 comprising SEQ ID NO:42. In preferred embodiments, the monoclonal anti-PD-L1 antagonist antibody, or antigen-binding portion thereof further comprises: (a) a light chain variable region CDR1 comprising SEQ ID NO:18; (b) a light chain variable region CDR2 comprising SEQ ID NO:24; and (c) a light chain variable region CDR3 comprising SEQ ID NO:30.

In one embodiment, the antibody or portion comprises a light chain variable region amino acid sequence having at least 95% identity to SEQ ID NO:6 and a heavy chain variable region amino acid sequence having at least 95% identity to SEQ ID NO:12. In another embodiment, the antibody or portion comprises a heavy chain variable region comprising an amino acid sequence that is at least 95%, at least 96%, at least 97%, at least 98%, or at least 99% identical to a sequence as set forth in SEQ ID NO:12.

In another aspect of the invention, an isolated monoclonal anti-PD-L1 antagonist antibody or an antigen-binding portion thereof comprises a heavy chain variable region comprising an amino sequence selected from the group consisting of SEQ ID NOs:65-67 and a light chain variable region comprising an amino sequence selected from the group consisting of SEQ ID NOs:49-51.

In another aspect of the invention, an isolated monoclonal anti-PD-L1 antagonist antibody or an antigen-binding portion thereof comprises: a heavy chain variable region comprising an amino sequence selected from the group consisting of SEQ ID NOs: 68-70 and a light chain variable region comprising an amino sequence selected from the group consisting of SEQ ID NOs:55-58.

In another aspect of the invention, an isolated monoclonal anti-PD-L1 antagonist antibody or an antigen-binding portion thereof comprises: a heavy chain variable region comprising an amino sequence selected from the group consisting of SEQ ID NOs: 71-76 and a light chain variable region comprising an amino sequence selected from the group consisting of SEQ ID NOs:59-61.

In another aspect of the invention, an isolated monoclonal anti-PD-L1 antagonist antibody or an antigen-binding portion thereof comprises: a heavy chain variable region comprising an amino sequence selected from the group consisting of SEQ ID NOs: 77-78 and a light chain variable region comprising an amino sequence selected from the group consisting of SEQ ID NOs:62-63.

In another aspect of the invention, an isolated monoclonal anti-PD-L1 antagonist antibody or an antigen-binding portion thereof comprises: a heavy chain variable region comprising an amino sequence selected from the group consisting of SEQ ID NOs: 79-80 and a light chain variable region comprising an amino sequence selected from the group consisting of SEQ ID NOs:64.

In another aspect of the invention, an isolated monoclonal anti-PD-L1 antagonist antibody or an antigen-binding portion thereof comprises: a heavy chain variable region comprising an amino sequence selected from the group consisting of SEQ ID NOs: 81-83 and a light chain variable region comprising an amino sequence selected from the group consisting of SEQ ID NOs:52-54.

In another aspect of the invention, an isolated monoclonal antibody or antigen binding portion thereof, comprising a light chain comprising an amino acid sequence selected from the group consisting of SEQ ID NOs: 84-99 and a heavy chain comprising an amino acid sequence selected from the group consisting of SEQ ID NOs: 100-118.

The antibodies of the disclosed invention can be further engineered into formats suitable for human therapeutics by modifications that minimize immunogenicity. Suitable antibodies include, but are not limited to chimeric antibodies and humanized antibodies. The affinity, stability and specificity of the disclosed antibodies can also be further optimized by techniques known to one of skill in the art. Other formats can involve oligomerization, drug conjugation and fusion of the disclosed antibodies with other functional proteins.

The antibodies of the disclosed invention can be, for example, full-length antibodies, for example of an IgG1, IgG2, IgG3, or IgG4 isotype. Alternatively, the disclosed antibodies can be antibody fragments, such as Fab, Fab' and F(ab')$_2$ fragments, diabody, triabody, tetrabody, single-chain variable region fragment (scFv), disulfide-stabilized variable region fragment (dsFv), and half antibodies. Alternatively, the disclosed antibodies can be bispecific antibodies.

In another aspect of the invention, the antibody or antigen-binding fragment thereof has an affinity (KD) for PD-L1 in the range of $5\times10^{-8}$ M to $1\times10^{-10}$ M, or $1.32\times10^{-9}$ M to $2.68\times10^{-10}$ M.

In some embodiments, the anti-PD-L1 antagonist antibody, or antigen-binding portion thereof binds to and blocks human PD-L1. Therefore the antibody, or antigen-binding portion can stimulate an anti-tumor immune response. In some embodiments, the anti-PD-L1 antagonist antibody, or antigen-binding portion thereof binds to and blocks non-human primate PD-L1.

In another aspect of the invention, a composition comprising the isolated anti-PD-L1 antagonist monoclonal antibody, or antigen-binding portion thereof is also provided.

In another aspect of the invention, a pharmaceutical composition comprising the isolated anti-PD-L1 antagonist monoclonal antibody, or antigen-binding portion thereof and a pharmaceutically acceptable carrier are also provided. Compositions comprising an immunoconjugate of the invention and a pharmaceutically acceptable carrier are also provided.

In another aspect of the invention, a vector comprising an isolated nucleic acid molecule encoding the antibody, or antigen-binding portion thereof, and a host cell comprising an expression vector comprising said nucleic acid molecule are also provided.

The present invention further provides a method of stimulating immune responses using the anti-PD-L1 antagonist antibodies of the disclosed invention. For example, in one embodiment, the disclosed invention provides a method for treating a subject in need thereof, comprising the step of administering to the subject an effective amount of the antibody or antigen-binding portion of the disclosed invention.

In another aspect, the disclosed invention provides a method for treating cancer in a human comprising the step of administering to the human the anti-PD-L1 antagonist antibody or antigen-binding portion of the disclosed invention in an amount effective to treat said cancer.

In another aspect, the disclosed invention provides a method for treating infectious diseases in a human comprising the step of administering to the human the anti-PD-L1 antagonist antibody or antigen-binding portion of the disclosed invention in an amount effective to treat said infectious diseases.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
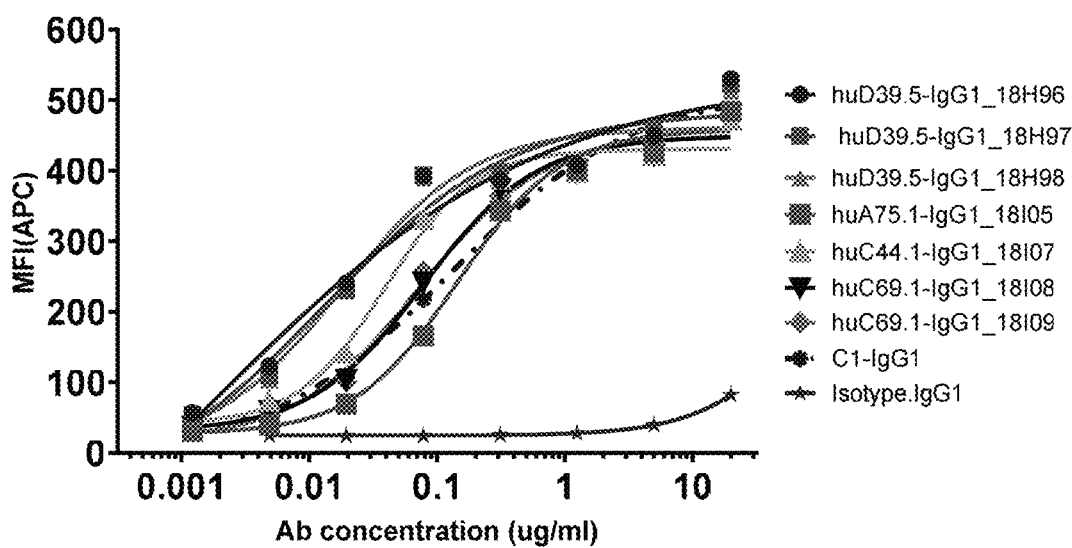
FIG. 1 shows Anti-PD-L1 Lead candidates bind to PD-L1 on A431 cells

The following embodiments and aspects thereof are described and illustrated in conjunction with systems, compositions and methods which are meant to be exemplary and illustrative, not limiting in scope.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, ±5%, ±1%, ±0.5% or ±0.1% from the specified value.

The term "epitope" as used herein can include any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the equilibrium dissociation constant is ≤1 μM, preferably ≤100 nM and most preferably ≤10 nM.

The term "$K_D$" can refer to the equilibrium dissociation constant of a particular antibody-antigen interaction.

The term "immune response" as used herein can refer to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from an organism of invading pathogens, cells or tissues infected with pathogens, cancerous cells, or, in cases of autoimmunity or pathological inflammation, normal organismal cells or tissues.

An "antigen-specific T cell response" as used herein can refer to responses by a T cell that result from stimulation of the T cell with the antigen for which the T cell is specific. Non-limiting examples of responses by a T cell upon antigen-specific stimulation include proliferation and cytokine production (e.g., IL-2 production).

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc region". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single region antibodies, chimeric antibodies, diabodies and polypeptides that contain at least a portion of an immunoglobulin that is sufficient to confer specific antigen binding to the polypeptide. The Fc region includes portions of two heavy chains contributing to two or three classes of the antibody. The Fc region may be produced by recombinant DNA techniques or by enzymatic (e.g. papain cleavage) or via chemical cleavage of intact antibodies.

The term "antibody fragment," as used herein, refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 regions; (ii) the Fab' fragment, which is a Fab fragment having one or more cysteine residues at the C-terminus of the CH1 region; (iii) the Fd fragment having VH and CH1 regions; (iv) the Fd' fragment having VH and CH1 regions and one or more cysteine residues at the C-terminus of the CH1 region; (v) the Fv fragment having the VL and VH regions of a single arm of an antibody; (vi) the dAb fragment (Ward et al., Nature 341, 544-546 (1989)) which consists of a VH region; (vii) isolated CDR regions; (viii) F(ab')2 fragments, a bivalent fragment including two Fab' fragments linked by a disulfide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable region (VH) connected to a light chain variable region (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

"Single-chain variable fragment", "single-chain antibody variable fragments" or "scFv" antibodies as used herein refers to forms of antibodies comprising the variable regions of only the heavy (VH) and light (VL) chains, connected by a linker peptide. The scFvs are capable of being expressed as a single chain polypeptide. The scFvs retain the specificity of the intact antibody from which it is derived. The light and heavy chains may be in any order, for example, VH-linker-VL or VL-linker-VH, so long as the specificity of the scFv to the target antigen is retained.

An "isolated antibody", as used herein, can refer to an antibody that is substantially free of other antibodies having different antigenic specificities (e.g., an isolated antibody that specifically binds a PD-L1 protein can be substantially free of antibodies that specifically bind antigens other than PD-L1 proteins). An isolated antibody that specifically binds a human PD-L1 protein can, however, have cross-reactivity to other antigens, such as PD-L1 proteins from other species. Moreover, an isolated antibody can be substantially free of other cellular material and/or chemicals.

Anti-PD-L1 antagonist antibody-producing cells, e.g., hybridomas, can be selected, cloned and further screened for desirable characteristics, including robust growth, high antibody production and desirable antibody characteristics. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

The terms "monoclonal antibody" or "monoclonal antibody composition" as used herein can refer to a preparation of antibody molecules of single molecular composition. A monoclonal antibody composition displays a single binding specificity and affinity for a particular epitope.

The term "recombinant human antibody", as used herein, can refer to all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" can refer to the antibody class (e.g., IgM or IgG1) that is encoded by the heavy chain constant region genes. An antibody can be an immunoglobulin G (IgG), an IgM, an IgE, an IgA or an IgD molecule, or is derived therefrom.

The phrases "an antibody recognizing an antigen" and "an antibody specific for an antigen" are used interchangeably herein with the term "an antibody which binds specifically to an antigen."

As used herein, an antibody that "specifically binds human PD-L1" can refer to an antibody that binds to a human PD-L1 protein (and possibly a PD-L1 protein from one or more non-human species) but does not substantially bind to non-PD-L1 proteins. Preferably, the antibody binds to a human PD-L1 protein with "high affinity," namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less.

The term "does not substantially bind" to a protein or cells, as used herein, can mean that it cannot bind or does not bind with a high affinity to the protein or cells, i.e., binds to the protein or cells with an $K_D$ of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "high affinity" for an IgG antibody can refer to an antibody having a $K_D$ of $1\times10^{-6}$ M or less, preferably $1\times10^{-7}$ M or less, more preferably $1\times10^{-8}$ M or less, even more preferably $1\times10^{-9}$ M or less, even more preferably $1\times10^{-10}$ M or less for a target antigen. However, "high affinity" binding can vary for other antibody isotypes.

The term "pharmaceutical formulation" refers to a preparation which is in such form as to permit the biological activity of an active ingredient contained therein to be effective, and which contains no additional components which are unacceptably toxic to a subject to which the formulation would be administered.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmaco-dynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

An "antagonist antibody" as used herein, is an antibody blocks or dampens a biological response by binding to and blocking a ligand (for example, PD-L1) to which the antibody binds. An antagonist may, for example, bind to PD-L1 and block the binding of PD-L1 with PD-1, which thereby inhibits PD-1 receptor's phosphorylation or may inhibit the signal/cells activation. In one embodiment, the antibodies of the invention are antagonistic anti-PD-L1 antibodies.

A "CDR grafted antibody" is an antibody comprising one or more CDRs derived from an antibody of a particular species or isotype and the framework of another antibody of the same or different species or isotype.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant regions of the heavy and/or light chains of the non-human species antibody are mutated to produce the humanized antibody. In another embodiment, the constant region(s) from a human antibody are fused to the variable region(s) of a non-human species. In another embodiment, a humanized antibody is a CDR grafted antibody comprising one or more CDRs derived from an antibody of a particular species or isotype and the framework of human antibodies. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" (cAb) refers to an antibody that contains one or more regions from one antibody and one or more regions from one or more other antibodies. In one embodiment, one or more of the PD-L1 are derived from a human anti-PD-L1 antibody. In another embodiment, all of the CDRs are derived from a human anti-PD-L1 antibody. In another embodiment, the CDRs from more than one human anti-PD-L1 antibodies are mixed and matched in a chimeric antibody. For instance, a chimeric antibody may comprise a CDR1 from the light chain of a first human anti-PD-L1 antibody, a CDR2 and a CDR3 from the light chain of a second human anti-PD-L1 antibody, and the CDRs from the heavy chain from a third anti-PD-L1 antibody. In the context of the present disclosure, cAbs represent variable regions of mouse monoclonal antibodies fused to the Fc regions of human antibodies. In another embodiment, other combinations are also possible.

The term "subject" can refer to any human or non-human animal. The subject can be male or female and can be any suitable age, including infant, juvenile, adolescent, adult, and geriatric subjects. The term "nonhuman animal" includes all vertebrates, e.g., mammals and non-mammals, such as nonhuman primates, sheep, dogs, cats, cows, horses, chickens, rabbits, mice, rats, amphibians, and reptiles, although mammals are preferred, such as non-human primates, sheep, dogs, cats, cows and horses.

The binding of an antibody of the disclosed invention to PD-L1 can be assessed using one or more techniques well established in the art. For example, in a preferred embodiment, an antibody can be tested by ELISA assays, for example using a recombinant PD-L1 protein. Still other suitable binding assays include but are not limited to a flow cytometry assay in which the antibody is reacted with a cell line that expresses human PD-L1, such as Expi293 or ExpiCHO cells that have been transfected to express PD-L1 (e.g., human PD-L1) on their cell surface. Additionally or alternatively, the binding of the antibody, including the binding kinetics (e.g., $K_D$ value) can be tested in BIAcore binding assays, Octet Red96 (Pall) and the like.

Preferably, an antibody of the disclosed invention binds to a human PD-L1 protein with a $K_D$ of $5\times10^{-8}$ M or less, binds to a human PD-L1 protein with a $K_D$ of $2\times10^{-8}$ M or less, binds to a human PD-L1 protein with a $K_D$ of $5\times10^{-9}$ M or less, binds to a human PD-L1 protein with a $K_D$ of $4\times10^{-9}$ M or less, binds to a human PD-L1 protein with a $K_D$ of $3\times10^{-9}$ M or less, binds to a human PD-L1 protein with a $K_D$ of $2\times10^{-9}$ M or less, binds to a human PD-L1 protein with a $K_D$ of $1\times10^{-9}$ M or less.

The present disclosure relates to isolated monoclonal antibodies, or antigen binding portions thereof, which binds to and blocks PD-L1, and uses thereof. In certain embodiments, the antibodies of the disclosed invention are derived from identified heavy and light chain germline sequences and/or comprise identified structural features such as CDR regions comprising identified amino acid sequences. This disclosure provides isolated antibodies, methods of making such antibodies and antigen-binding portions thereof of the disclosed invention. This disclosure also relates to methods of using the antibodies, such as using the anti-PD-L1 antibodies of the disclosed invention to stimulate immune responses, alone or in combination with other immunostimulatory or therapeutic antibodies. Accordingly, also provided are methods of using the anti-PD-L1 antagonist antibodies of the disclosed invention for example, including but not limited to, treating cancer in a human. Various aspects of the invention relate to antibodies and antibody fragments, pharmaceutical compositions, nucleic acids, recombinant expression vectors, and host cells for making such antibodies and fragments. Methods of using the antibodies of the invention to detect human PD-L1, to inhibit PD-L1 activity, either in vitro or in vivo, and to prevent or treat disorders such as cancer are also encompassed by the invention.

Complementarity determining regions (CDRs) are known as hypervariable regions both in the light chain and the heavy chain variable regions. The more highly conserved portions of variable regions are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable region sequences that is applicable to any antibody. One of ordinary skill in the art can unambiguously assign this system of "Kabat numbering" to any variable region amino acid sequence, without reliance on any experimental data beyond the sequence itself.

In certain embodiment, the present invention provides anti-PD-L1 antagonist antibodies or antigen-binding portions thereof. In one embodiment, the mouse antibody or portion comprises (a) a light chain variable region CDR1 comprising SEQ ID NO:13, SEQ ID NO:14, SEQ ID NO:15, SEQ ID NO:16; SEQ ID NO:17, SEQ ID NO:18, (b) a light chain variable region CDR2 comprising SEQ ID NO:19, SEQ ID NO:20, SEQ ID NO:21, SEQ ID NO:22, SEQ ID NO:23, SEQ ID NO:24; (c) a light chain variable region CDR3 comprising SEQ ID NO:25, SEQ ID NO:26, SEQ ID NO:27, SEQ ID NO:28, SEQ ID NO:29, SEQ ID NO:30; (d) a heavy chain variable region CDR1 comprising SEQ ID NO:31, SEQ ID NO:32, SEQ ID NO:33, SEQ ID NO:34, SEQ ID NO:35, SEQ ID NO:36; (e) a heavy chain variable region CDR2 comprising SEQ ID NO:37, SEQ ID NO:38, SEQ ID NO:39, SEQ ID NO:40, SEQ ID NO:41, SEQ ID NO:42; (f) a heavy chain variable region CDR3 comprising SEQ ID NO:43, SEQ ID NO:44, SEQ ID NO:45, SEQ ID NO:46, SEQ ID NO:47, SEQ ID NO:48.

In one embodiment, the present disclosure provides a monoclonal antibody or antigen-binding portion thereof that binds to a PD-L1 epitope, that comprises a light chain variable region amino acid sequence having at least 95% identity to SEQ ID NOs: 1, 49, 50 or 51; and a heavy chain variable region amino acid sequence having at least 95% identity to SEQ ID NOs: 7, 65, 66 or 67.

In another embodiment, the present disclosure provides a monoclonal antibody or antigen-binding portion thereof that binds to a PD-L1 epitope, that comprises a light chain variable region amino acid sequence having at least 95% identity to SEQ ID NOs: 2, 55, 56, 57 or 58; and a heavy chain variable region amino acid sequence having at least 95% identity to SEQ ID NOs: 8, 68, 69 or 70

In yet another embodiment, the present disclosure provides a monoclonal antibody or antigen-binding portion thereof that binds to a PD-L1 epitope, that comprises a light chain variable region amino acid sequence having at least 95% identity to SEQ ID NOs: 3, 59, 60 or 61 and a heavy chain variable region amino acid sequence having at least 95% identity to SEQ ID NOs: 9, 71, 72, 73, 74, 75 or 76.

In yet another embodiment, the present disclosure provides a monoclonal antibody or antigen-binding portion thereof that binds to a PD-L1 epitope, that comprises a light chain variable region amino acid sequence having at least 95% identity to SEQ ID NOs: 4, 62 or 63 and a heavy chain variable region amino acid sequence having at least 95% identity to SEQ ID NOs: 10, 77 or 78.

In yet another embodiment, the present disclosure provides a monoclonal antibody or antigen-binding portion thereof that binds to a PD-L1 epitope, that comprises a light chain variable region amino acid sequence having at least 95% identity to SEQ ID NOs: 5 or 64 and a heavy chain variable region amino acid sequence having at least 95% identity to SEQ ID NOs: 11, 79 or 80.

In yet another embodiment, the present disclosure provides a monoclonal antibody or antigen-binding portion thereof that binds to a PD-L1 epitope, that comprises a light chain variable region amino acid sequence having at least 95% identity to SEQ ID NOs: 6, 52, 53 or 54 and heavy chain variable region amino acid sequence having at least 95% identity to SEQ ID NOs: 12, 81, 82 or 83.

Given that each of these antibody Fabs can bind to human PD-L1, the VH and VL sequences can be "mixed and matched" to create other anti-PD-L1 binding molecules of the invention. Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

In some embodiments, the humanized anti-PD-L1 antibody or antigen binding portion thereof comprises a heavy chain variable region comprising an amino acid sequence selected from the group consisting of SEQ ID NOs: 65-67 and a light chain variable region comprising an amino acid sequence selected from the group consisting of SEQ ID NOs: 49-51. Preferred heavy and light chain combinations include but not limited to:

(a) a heavy chain variable region comprising the amino acid sequence of SEQ ID NO:65 and a light chain variable region comprising the amino acid sequence of SEQ ID NO:49;

(b) a heavy chain variable region comprising the amino acid sequence of SEQ ID NO:66 and a light chain variable region comprising the amino acid sequence of SEQ ID NO:50;

(c) a heavy chain variable region comprising the amino acid sequence of SEQ ID NO:67 and a light chain variable region comprising the amino acid sequence of SEQ ID NO:51;

In some embodiments, the humanized anti-PD-L1 antibody or antigen binding portion thereof comprises a heavy chain variable region comprising an amino acid sequence selected from the group consisting of SEQ ID NOs: 68-70 and a light chain variable region comprising an amino acid sequence selected from the group consisting of SEQ ID NOs: 55-58. Preferred heavy and light chain combinations include but not limited to:

(a) a heavy chain variable region comprising the amino acid sequence of SEQ ID NO:68 and a light chain variable region comprising the amino acid sequence of SEQ ID NO:55;

(b) a heavy chain variable region comprising the amino acid sequence of SEQ ID NO:69 and a light chain variable region comprising the amino acid sequence of SEQ ID NO:56;

(c) a heavy chain variable region comprising the amino acid sequence of SEQ ID NO:70 and a light chain variable region comprising the amino acid sequence of SEQ ID NO:57;

In some embodiments, the humanized anti-PD-L1 antibody or antigen binding portion thereof comprises a heavy chain variable region comprising an amino acid sequence selected from the group consisting of SEQ ID NOs: 71-76 and a light chain variable region comprising an amino acid sequence selected from the group consisting of SEQ ID NOs: 59-61. Preferred heavy and light chain combinations include but not limited to:

(a) a heavy chain variable region comprising the amino acid sequence of SEQ ID NO:71 and a light chain variable region comprising the amino acid sequence of SEQ ID NO:59;

(b) a heavy chain variable region comprising the amino acid sequence of SEQ ID NO:72 and a light chain variable region comprising the amino acid sequence of SEQ ID NO:60;

(c) a heavy chain variable region comprising the amino acid sequence of SEQ ID NO:73 and a light chain variable region comprising the amino acid sequence of SEQ ID NO:61;

In some embodiments, the humanized anti-PD-L1 antibody or antigen binding portion thereof comprises a heavy chain variable region comprising an amino acid sequence selected from the group consisting of SEQ ID NOs: 77-78 and a light chain variable region comprising an amino acid sequence selected from the group consisting of SEQ ID NOs: 62-63. Preferred heavy and light chain combinations include but not limited to:

(a) a heavy chain variable region comprising the amino acid sequence of SEQ ID NO:77 and a light chain variable region comprising the amino acid sequence of SEQ ID NO: 62;

(b) a heavy chain variable region comprising the amino acid sequence of SEQ ID NO:78 and a light chain variable region comprising the amino acid sequence of SEQ ID NO: 63;

In some embodiments, the humanized anti-PD-L1 antibody or antigen binding portion thereof comprises a heavy chain variable region comprising an amino acid sequence selected from the group consisting of SEQ ID NOs: 79-80 and a light chain variable region comprising an amino acid sequence selected from the group consisting of SEQ ID NOs: 64. Preferred heavy and light chain combinations include but not limited to:

(a) a heavy chain variable region comprising the amino acid sequence of SEQ ID NO:79 and a light chain variable region comprising the amino acid sequence of SEQ ID NO:64;

In some embodiments, the humanized anti-PD-L1 antibody or antigen binding portion thereof comprises a heavy chain variable region comprising an amino acid sequence selected from the group consisting of SEQ ID NOs:81-83 and a light chain variable region comprising an amino acid sequence selected from the group consisting of SEQ ID NOs:52-54. Preferred heavy and light chain combinations include but not limited to:

(a) a heavy chain variable region comprising the amino acid sequence of SEQ ID NO:81 and a light chain variable region comprising the amino acid sequence of SEQ ID NO:52;

(b) a heavy chain variable region comprising the amino acid sequence of SEQ ID NO:82 and a light chain variable region comprising the amino acid sequence of SEQ ID NO:53;

(c) a heavy chain variable region comprising the amino acid sequence of SEQ ID NO:83 and a light chain variable region comprising the amino acid sequence of SEQ ID NO:54;

In some embodiments, the humanized anti-PD-L1 antibody or antigen binding portion thereof comprises a light chain comprising an amino acid sequence selected from the group consisting of SEQ ID NOs:84-99 and a heavy chain comprising an amino acid sequence selected from the group consisting of SEQ ID NOs:100-118.

In one embodiment, the invention provides an anti-PD-L1 antibody, or an antigen-binding fragment thereof, comprising a heavy chain comprising a CDR3 region as set forth in SEQ ID NO: 43 and comprising a heavy chain variable region comprising an amino acid sequence that has at least 95%, at least 96%, at least 97%, at least 98%, or at least 99% identical to a sequence as set forth in any one of SEQ ID NOs: 7 or 65-67.

In one embodiment, the invention provides an anti-PD-L1 antibody, or an antigen-binding fragment thereof, comprising a heavy chain comprising a CDR3 region as set forth in SEQ ID NO: 44, and comprising a heavy chain variable region comprising an amino acid sequence that has at least 95%, at least 96%, at least 97%, at least 98%, or at least 99% identical to a sequence as set forth in any one of SEQ ID NOs:8 or 68-70.

In one embodiment, the invention provides an anti-PD-L1 antibody, or an antigen-binding fragment thereof, comprising a heavy chain comprising a CDR3 region as set forth in SEQ ID NO: 45, and comprising a heavy chain variable region comprising an amino acid sequence that has at least 95%, at least 96%, at least 97%, at least 98%, or at least 99% identical to a sequence as set forth in any one of SEQ ID NOs: 9 or 71-76.

In one embodiment, the invention provides an anti-PD-L1 antibody, or an antigen-binding fragment thereof, comprising a heavy chain comprising a CDR3 region as set forth in SEQ ID NO: 46, and comprising a heavy chain variable region comprising an amino acid sequence that has at least 95%, at least 96%, at least 97%, at least 98%, or at least 99% identical to a sequence as set forth in any one of SEQ ID NOs: 10 or 77-78.

In one embodiment, the invention provides an anti-PD-L1 antibody, or an antigen-binding fragment thereof, comprising a heavy chain comprising a CDR3 region as set forth in SEQ ID NO: 47, and comprising a heavy chain variable region comprising an amino acid sequence that has at least 95%, at least 96%, at least 97%, at least 98%, or at least 99% identical to a sequence as set forth in any one of SEQ ID NOs: 11 or 79-80.

In one embodiment, the invention provides an anti-PD-L1 antibody, or an antigen-binding fragment thereof, comprising a heavy chain comprising a CDR3 region as set forth in SEQ ID NO: 48, and comprising a heavy chain variable region comprising an amino acid sequence that has at least 95%, at least 96%, at least 97%, at least 98%, or at least 99% identical to a sequence as set forth in any one of SEQ ID NOs: 12 or 81-83.

In one embodiment, the invention provides an anti-PD-L1 antibody, or an antigen-binding fragment thereof, comprising a light chain comprising a CDR3 region as set forth in SEQ ID NO: 25, and having a light chain variable region comprising an amino acid sequence that has at least 95%, at least 96%, at least 97%, at least 98%, or at least 99% identical to a sequence as set forth in any one of SEQ ID NOs: 1 or 49-51.

In one embodiment, the invention provides an anti-PD-L1 antibody, or an antigen-binding fragment thereof, comprising a light chain comprising a CDR3 region as set forth in SEQ ID NO: 26, and having a light chain variable region comprising an amino acid sequence that has at least 95%, at least 96%, at least 97%, at least 98%, or at least 99% identical to a sequence as set forth in any one of SEQ ID NOs: 2 or 55-58.

In one embodiment, the invention provides an anti-PD-L1 antibody, or an antigen-binding fragment thereof, comprising a light chain comprising a CDR3 region as set forth in SEQ ID NO: 27, and having a light chain variable region comprising an amino acid sequence that has at least 95%, at least 96%, at least 97%, at least 98%, or at least 99% identical to a sequence as set forth in any one of SEQ ID NOs: 3 or 59-61.

In one embodiment, the invention provides an anti-PD-L1 antibody, or an antigen-binding fragment thereof, comprising a light chain comprising a CDR3 region as set forth in SEQ ID NO: 28, and having a light chain variable region comprising an amino acid sequence that has at least 95%, at least 96%, at least 97%, at least 98%, or at least 99% identical to a sequence as set forth in any one of SEQ ID NOs: 4 or 62-63.

In one embodiment, the invention provides an anti-PD-L1 antibody, or an antigen-binding fragment thereof, comprising a light chain comprising a CDR3 region as set forth in SEQ ID NO: 29, and having a light chain variable region comprising an amino acid sequence that has at least 95%, at least 96%, at least 97%, at least 98%, or at least 99% identical to a sequence as set forth in any one of SEQ ID NOs: 5 or 64.

In one embodiment, the invention provides an anti-PD-L1 antibody, or an antigen-binding fragment thereof, comprising a light chain comprising a CDR3 region as set forth in SEQ ID NO: 30, and having a light chain variable region comprising an amino acid sequence that has at least 95%, at least 96%, at least 97%, at least 98%, or at least 99% identical to a sequence as set forth in any one of SEQ ID NOs: 6 or 52-54.

Thus, in certain embodiments, the CDR3 region is held constant, while variability may be introduced into the remaining CDRs and/or framework regions of the heavy and/or light chains, while the antibody, or antigen binding fragment thereof, retains the ability to bind to PD-L1 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In addition to chemically-conserved amino acids, substitutions may include any amino acid which occurs in similar positions within related evolutionary-conserved human variable heavy chain sequences, human variable light chain sequences, and orthologous sequences from non-human species.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Working Examples

The following examples are not intended to limit the scope of the claims to the invention but is rather intended to be exemplary of certain embodiments. Any variations in the exemplified methods which occur to the skilled artisan are intended to fall within the scope of the present invention.

Vector Construction:

Vector pcDNA3.4TOPO (Invitrogen) was ligated to a short polylinker containing EcoRI, XhoI, and NotI. The resulting plasmid was digested with EcoRI and NotI restriction enzymes and purified by gel electrophoresis. For heavy chain cloning, we assembled using Gibson assembly the prepared vector, a gblock encoding and VH region (IDT), and human IgG2 gblock encoding an XhoI site at the junction of the J-chain and CH1 domain. The plasmid was prepared and digested with EcoRI and XhoI to accommodate all the humanized variable heavy (VH) domains with an IgG2 isotype. All assembly was done with the Gibson method (NEB). Variable light regions were constructed with a similar method using gblocks to assemble Vkappa regions with a gblock fragment which encoded the constant kappa (Ck).

Protein Expression, Purification, and Binding Characterization:

Plasmids were prepped and transfected into Expi293 or ExpiCHO cells using the transient expression system (Thermo Fisher). Briefly plasmids were transfected into 3e6 cells/ml cells at 1 ug plasmid DNA total/ml culture. Heavy chain and light chain plasmids were mixed in a 1:1 ratio. Cultures were incubated at 37° C., shaking. After 16 hours, we added Transfection Enhancer 1 and 2 to the cultures and continued incubation for six days. Supernatant were filtered, and protein titers were determined by an IgG quantitation protocol using the Octet Red96 (Pall). IgG was purified by Mab Select Sure Protein-A column purification on an ACTA PURE system and dialyzed overnight in PBS. Purified antibodies were characterized for affinity to the antigen by Octet Red96 by loading purified antibodies onto anti-human Heavy Chain (AHC) capture sensors and measuring rates of association and dissociation of PDL1 histidine tagged target at three concentrations. (Table 1).

TABLE 1

Mono-valent binding kinetics of humanized anti-PD-L1 Antibodies were compared to benchmark controls as determined by Octet.

Figure 2:
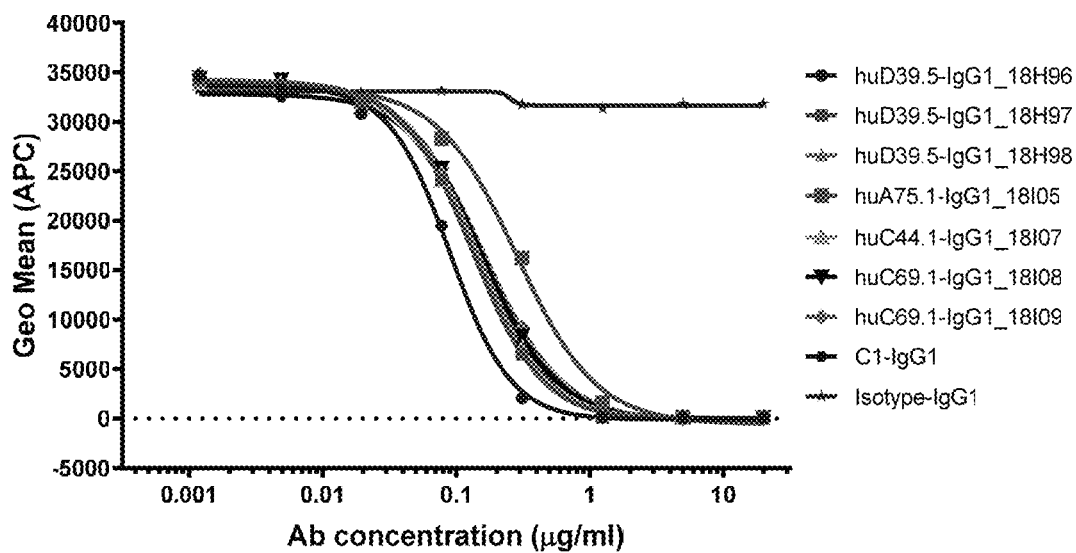
FIG. 2 shows Anti-PD-L1 Lead candidates block PD-1 interaction on HEK293/huPD-L1 cells.

| Loading Sample ID | % Monomer | KD (M) | kon(1/Ms) | kdis(1/s) | T½ (min) |
|---|---|---|---|---|---|
| huD39.5_IgG1_1 | 99.6 | 1.13E−09 | 5.17E+05 | 5.84E−04 | 19.8 |
| huD39.5_IgG1_2 | 99.8 | 1.13E−09 | 6.42E+05 | 7.24E−04 | 16 |
| huA75.1_IgG1 | 97.5 | 2.68E−10 | 3.12E+05 | 8.34E−05 | 138.5 |
| huC44.1_IgG1 | 100 | 1.32E−09 | 4.89E+05 | 6.46E−04 | 17.9 |
| huC69.1_IgG1 | 100 | 1.12E−09 | 4.52E+05 | 5.05E−04 | 22.9 |
| C2-IgG1 | | 6.29E−10 | 4.66E+05 | 2.94E−04 | 39.3 |
| C1-IgG1 | | 8.72E−10 | 3.62E+05 | 3.15E−04 | 36.7 | bodies were compared with the same assay using rhPD-1 Fc-biotin at 0.5 ug/ml final concentration and detection with Streptavidin-APC (R&D cat #F0050) (FIG. 2) (Table 2).

TABLE 2

EC50 and IC50 values for lead candidates

| Antibody | Binding EC50 (ug/ml) | | | PD-1 Blocking IC50 (ug/ml) |
|---|---|---|---|---|
| | HEK293/ huPD-L1 | HEK293/ cynoPD-L1 | A431 | HEK293/ huPD-L1 |
| C1-IgG1 | 0.182 | 0.065 | 0.131 | 0.15 |
| huD39.5_IgG1_1 | 0.104 | 0.032 | 0.002 | 0.09 |
| huD39.5_IgG1_2 | 0.091 | 0.044 | 0.018 | 0.146 |
| huA75.1_IgG1 | 0.205 | 0.125 | 0.145 | 0.286 |
| huC44.1_IgG1 | 0.164 | 0.044 | 0.04 | 0.138 |
| huC69.1_IgG1 | 0.268 | 0.054 | 0.079 | 0.153 |

SEB Stimulation Assay

Fresh PBMCs were diluted to 2E6 cells/ml in X-Vivo 15 medium (Lonza cat #04-744Q). SEB (Millipore cat Flow Cytometry Binding Analysis of Anti-PD-L1 Antibodies to PD-L1 Expressing A431 Cancer Cells Two days prior to the FACS analysis, A431 cancer cells were seeded into 24-well plates at 30-60% confluence in the absence or the presence of 1000 U/ml of recombinant human IFN-γ to stimulate PD-L1 expression. On the day of the FACS analysis, wells were washed with PBS and harvested with Trypsin/EDTA. Detached cells were washed twice, resuspended in FACS buffer at 5E6 cells/ml, and aliquoted into in 96 well plates at 1E5 cells/well. Cells were stained with 5 ug/ml anti-PD-L1 antibodies, positive control antibody "C1-IgG1", or isotype IgG1 on ice for 45 minutes followed by washing and secondary staining with 1:500 diluted Goat anti-human IgG-AF647. Cells were analyzed by flow cytometry following a final wash and addition of 7-AAD (FIG. 1).

PD-1 His Tag Blocking Assay on hPDL1/HEK293 Cells Testing Humanized Anti-PD-L1

For screening hybridomas, hPD-L1 expressing 293 cells were harvested by Accutase and resuspend at 4E6 cells/ml cells with FACS Wash buffer. To compare blocking abilities of antibodies, we mixed 30 ul cells/well (120,000), 30 ul of 6 ug/ml rhPD-1 His tag protein (2 ug/ml final concentration), and 30 ul of serially titrated anti-PDL1 antibodies and incubated for 20 min on ice. Following incubation, cells were washed and bound PD-1 was detected with anti-His Tag-APC Mouse IgG1 (R&D Cat #IC050A). Cells were analyzed by flow cytometry following a final wash and addition of 7-AAD. Blocking abilities of humanized anti-

Figure 3:
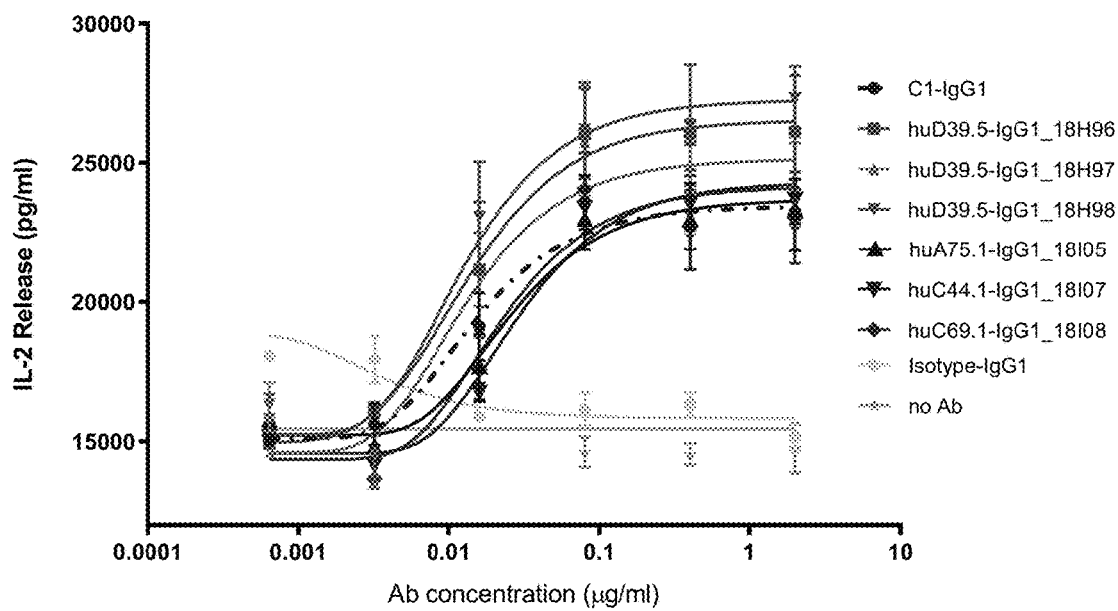
FIG. 3 show Anti-PD-L1 antibodies potentiated IL-2 release by SEB stimulation FIG. 4 show PD-L1 Antibodies Potentiated IFN gamma Secretion in Mixed Lymphocyte Reaction Assays indicating that the lead anti-PD-L1 antibodies blocked PD-1-mediated inhibition.

324798) was added to the PBMCs at 200 ng/ml (2×). Cells were treated with antibodies by adding 100 ul of diluted antibodies and 100 ul of PBMC/SEB antigen mixture into 96-well flat-bottom plates. Following incubation at 37° C. for 48 hours, supernatants were analyzed for IL-2 with an ELISA kit (R&D Systems) (FIG. 3).

Mixed Lymphocyte Reaction Assay

PBMCs were isolated from human buffy coat using Density Gradient Centrifugation (Miltenyi Biotec) and washed 4 times with PBS. CD4+ T cells were isolated (Miltenyi Biotec cat #130-096-533) from the PBMCs and resuspended in X-Vivo 15 medium at 4E6 cells/ml.

Monocyte-derived dendritic cells were generated from positively selected CD14+ monocytes (Monocyte Isolation Kit II, Cat no. 130-091-153, Miltenyi Biotec). Cells were seeded at 5E5 cells/ml in complete RPMI-1640 media supplemented with 10% fetal bovine serum (FBS) for 7 days. Cultures were supplemented with recombinant human (rh-) IL-4 (1000 U/ml) (R&D Systems) and rh granulocyte-macrophage colony-stimulating factor (rh-GMCSF) (500 U/ml) (R&D Systems) on days 0, 2 and 5. Immature DCs were harvested on Day 7 and resuspended in 5 ml RPMI-1640, 10% FBS medium. Cells were incubated with occasional mixing with 20 ug/ml mitomycin C (Roche REF 10107409001) for 1 hour at 37° C. followed by washing and resuspension in X-Vivo 15 media to 4E5 cells/ml.

In 96 well flat bottom plates, we mixed 50 ul DC cells (2E4 DCs/well), 100 ul serial diluted anti-PD-L1 antibodies, and controls at a 2× concentration, and 50 ul purified CD4+

Figure 4:
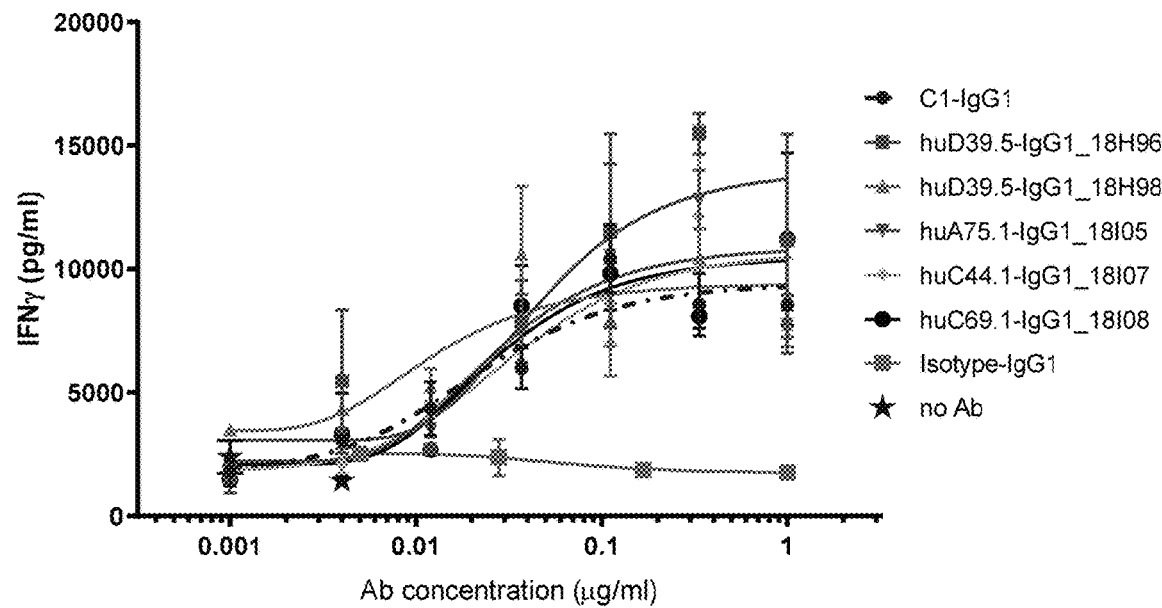

T cells (2E5 CD4+ T cells/per well) at 1:10 ratio (DCs:T cells). Plates were incubated for 5 days and the supernatants were analyzed by ELISA for IFNg release (R&D Systems) (FIG. 4).

CMV Antigen Recall Response In Vitro with Anti-PDL1 Treatment

Figure 5:
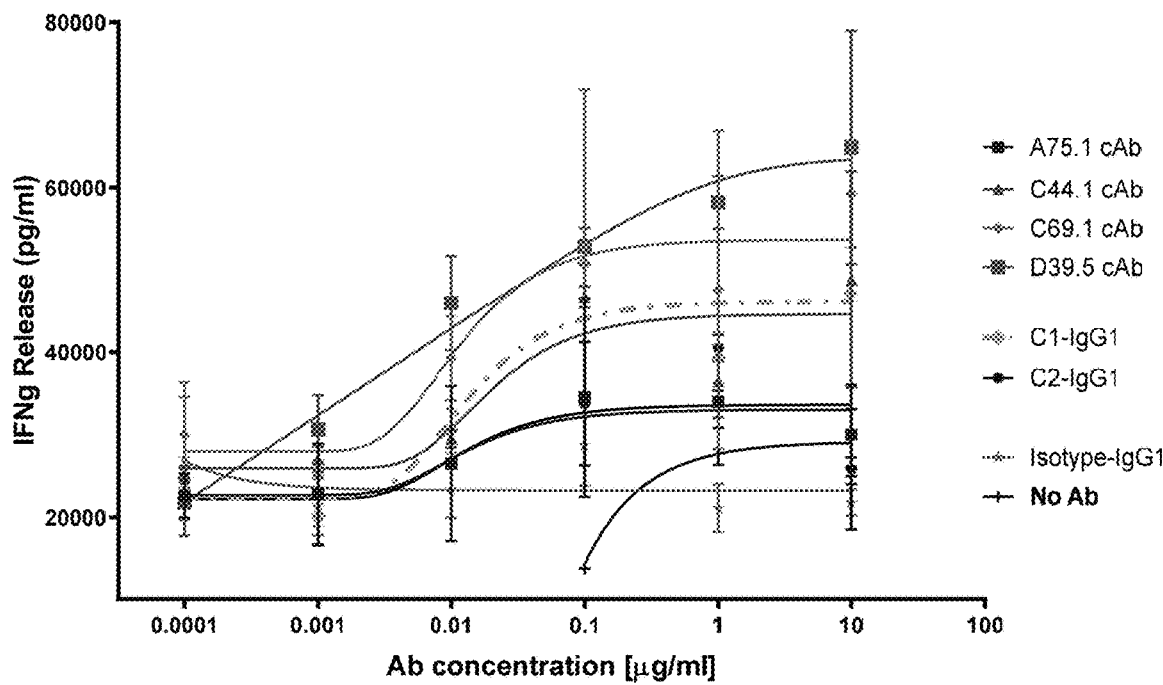
FIG. 5 shows PD-L1 blockade by lead antibodies enhanced interferon gamma production by T cells in CMV peptide-specific recall response assays.

Thawed PBMCs from a CMV+ donor (Astarte Biologics) were counted and resuspended in AIM-V medium with β-Mercaptoethanol (1:1000) at 2E6 cells/ml. In a 96-well flat-bottom plate, we mixed 100 ul CMV+ PBMCs (2E5 cells/well), 50 ul of 5 ug/ml CMV antigen (Astarte cat #1004), and 50 ul serially diluted anti-PDL1 antibodies and controls. Plates were incubated for 4 days and the supernatants were analyzed by ELISA for IFNg release (R&D Systems) (FIG. 5).

Protein Thermal Shift of Humanized Anti-PDL1 Antibodies

Figure 6:
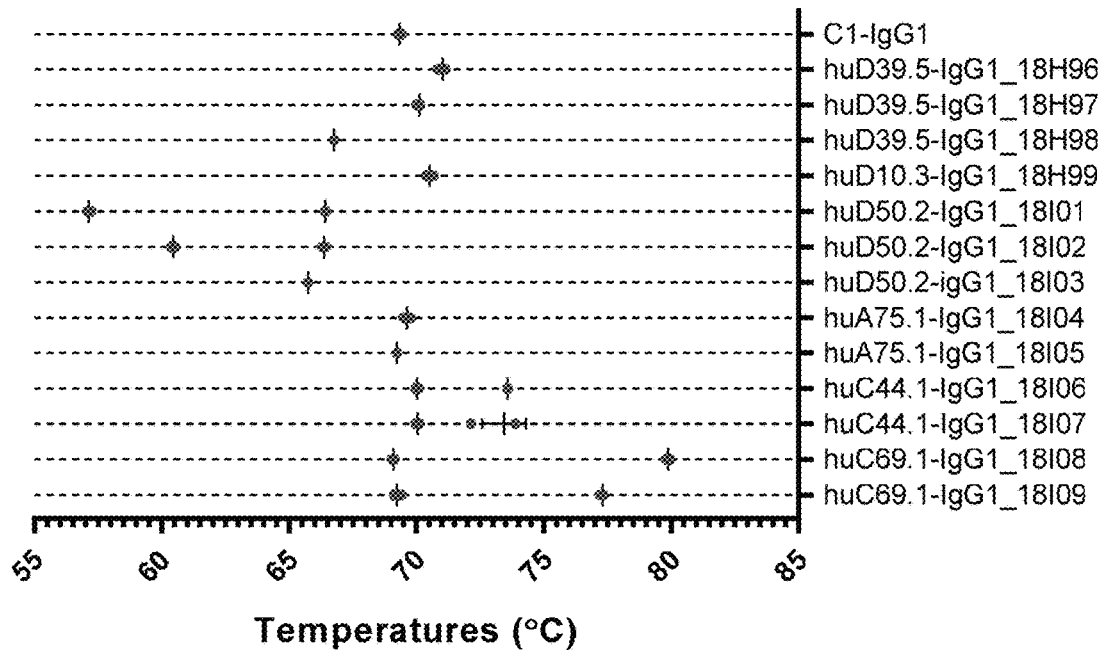
FIG. 6 shows thermal stability of humanized anti-PD-L1 lead antibodies

Ten (10) ug/ml anti-PD-L1 antibodies were mixed with 2 ul 50× protein thermal shift dye, and PBS to a final volume of 100 ul. Samples were aliquoted into a PCR 96-tube plate in quadruplicate (25 ul/well). Protein Thermal Shift reactions were measured on an Applied Biosystems StepOne Real-Time PCR instrument using a continuous temperature gradient of 1° C. change per 1 min 5 sec from 22-95° C. Tm was analyzed using the derivative method (FIG. 6).

```
Sequence Listing
Mouse antibodies
                                                      SEQ ID NO: 1
DIQMTQSPASLSVSVGETVTITCRASENIHSNLAWYQQKQGKSPQLLVYGATNLADGVPSRFSG SGSGAQYSLKINSLQSEDFGSYYCQHFWGTPPYAFGGGTKLETK
Underlined and bold: CDR1, 2 and 3, respectively (the same below),
defined according to the Kabat numbering scheme.

SEQ ID NO: 2
QIVLTQSPAIMSASPGEKVTISCSASSSVFDMYWYQQKPGSSPKPWIYRTSNLASGVPARFSGSGS

GTSYFLTISSMEAEDAATYYCQQYQSFPLTFGAGTKLELK

SEQ ID NO: 3
DIQMTQSPSSLSASLGERVSLICRASQEISGYLSWLQQKSDGTIKRLIFAASTLDPGVPKRFSGSRS

GADYSLTISSLESEDFADYYCLQYAIYPPTFGSGTKLEIK

SEQ ID NO: 4
QIVLTQSPAIMSASPGEKVTMTCSASSSVSFMHWYQQKSGTSPKKWIYDTSKLASGVPVRFSGS

GSGTSYSLTIINMEAEDAATYYCQQWTYYPPTFGGGTKLEIK

SEQ ID NO: 5
DIQMTQSPSSLSASLGERVSLTCRASQEISVYLSWLQQKPDGTIKRLIYAASTLDSGVPQRFRGSR

SGSDYSLTISSLESEDFADYYCVQYTSHPYTFGGGTKLEIK

SEQ ID NO: 6
DIQMTQSPASLSVSVGETVTITCRASENIHSNLAWYQQKQGKSPQLLVYGATNLADGVPSRFSG

SGSGAQYSLKINSLQSEDFGSYYCQHFWGTPPYVFGGGTKLETK

SEQ ID NO: 7
QVQLQQPGSELVRPGTSVKLSCKASGYTFTTFWMHWVKQRPGQGLEWIGNIYPGSGTINYDE

KFRSKATLTVDTSSNTAYMQVSSLTSEDSAVYYCTTGWDGEHWGQGTTLTVSS

SEQ ID NO: 8
EVQLVESGGGLVKPGGSLKLSCAASGFTFSDYGMHWIRQAPEKGLEWIAYIGTTSSIIYYADTV

KGRFTISRDNAKNTLFLQMTSLRSEDTAMYYCARRDYGNYYWYLDVWGTGTTVTVSS

SEQ ID NO: 9
EVQLQQSGAELVKPGASVKLSCTASGFNIKDTYMHWVQQRPEQGLEWIGRIDPMNGNSKYDP

KFQDKATITADTSSNTAYLQLSSLTSEDTAVYYCTSSKWGDYWGQGTTLTVSS

SEQ ID NO: 10
EVQLQQSGAELVRPGALVKVSCKASGFNIKDYYIHWVKQRPEQGLEWIGWIDPDNGNTKYDP

NFQGKASMTADTSSNTVNLQLSSLTSKDTAVYYCARYGGYGGFYTMDYWGQGTSVTVSS

SEQ ID NO: 11
QVQLQQPGTELVKPGASVKLSCKASGYTFTIYWMHWVKQRPGRGLEWIGRIDPNSGDTKYTE

KFKNRATLTVDKSSNTAYMQFSSLASDDSAVYYCARGGPNWDGFAYWGQGTLVTVSA

SEQ ID NO: 12
QVQLQQPRSELVRPGASVKLSCKASGYTFTTFWMHWVKQRPGQGLEWIGNIYPGSGISNYDEK

FKNKATLTVDTSSSTAYMQVSSLTSEDSAVYYCTTGWDGEHWGQGTTLTVSS
```

-continued

Light Chain CDRs
CDR1

| | |
|---|---|
| RASENIHSNLA | SEQ ID NO: 13 |
| SASSSVFDMY | SEQ ID NO: 14 |
| RASQEISGYLS | SEQ ID NO: 15 |
| SASSSVSFMH | SEQ ID NO: 16 |
| RASQEISVYLS | SEQ ID NO: 17 |
| RASENIHSNLA | SEQ ID NO: 18 |

CDR2

| | |
|---|---|
| GATNLAD | SEQ ID NO: 19 |
| RTSNLAS | SEQ ID NO: 20 |
| AASTLDP | SEQ ID NO: 21 |
| DTSKLAS | SEQ ID NO: 22 |
| AASTLDS | SEQ ID NO: 23 |
| GATNLAD | SEQ ID NO: 24 |

CDR3

| | |
|---|---|
| QHFWGTPPYA | SEQ ID NO: 25 |
| QQYQSFPLT | SEQ ID NO: 26 |
| LQYAIYPPT | SEQ ID NO: 27 |
| QQWTYYPPT | SEQ ID NO: 28 |
| VQYTSHPYT | SEQ ID NO: 29 |
| QHFWGTPPYV | SEQ ID NO: 30 |

Heavy Chain CDRs
CDR1

| | |
|---|---|
| TFWMH | SEQ ID NO: 31 |
| DYGMH | SEQ ID NO: 32 |
| DTYMH | SEQ ID NO: 33 |
| DYYIH | SEQ ID NO: 34 |
| IYWMH | SEQ ID NO: 35 |
| TFWMH | SEQ ID NO: 36 |

CDR2

| | |
|---|---|
| NIYPGSGTINYDEKFRS | SEQ ID NO: 37 |

-continued

YIGTTSSIIYYADTVKG
SEQ ID NO: 38

RIDPMNGNSKYDPKFQD
SEQ ID NO: 39

WIDPDNGNTKYDPNFQG
SEQ ID NO: 40

RIDPNSGDTKYTEKFKN
SEQ ID NO: 41

NIYPGSGISNYDEKFKN
SEQ ID NO: 42

CDR3

GWDGEH
SEQ ID NO: 43

RDYGNYYWYLDV
SEQ ID NO: 44

SKWGDY
SEQ ID NO: 45

YGGYGGFYTMDY
SEQ ID NO: 46

GGPNWDGFAY
SEQ ID NO: 47

GWDGEH
SEQ ID NO: 48

Humanized light chain variable domain

SEQ ID NO: 49
DIQMTQSPSSLSASVGDRVTITCRASENIHSNLAWYQQKPGKAPKLLVYGATNLADGVPSRFSG
SGSGAQYTLTISSLQPEDFATYYCQHFWGTPPYAFGGGTKLEIK

SEQ ID NO: 50
DIQMTQSPSSLSASVGDRVTITCRASENIHSNLAWYQQKPGKAPQLLVYGATNLADGVPSRFSG
SGSGAQYTLTISSLQPEDFATYYCQHFWGTPPYAFGGGTKLEIK

SEQ ID NO: 51
DIQMTQSPSSLSVSVGDRVTITCRASENIHSNLAWYQQKPGKAPQLLVYGATNLADGVPSRFSG
SGSGAQYTLTISSLQPEDFATYYCQHFWGTPPYAFGGGTKLEIK

SEQ ID NO: 52
DIQMTQSPSSLSASVGDRVTITCRASENIHSNLAWYQQKPGKAPKLLVYGATNLADGVPSRFSG
SGSGAQYTLTISSLQPEDFATYYCQHFWGTPPYVFGGGTKLEIK

SEQ ID NO: 53
DIQMTQSPSSLSASVGDRVTITCRASENIHSNLAWYQQKPGKAPQLLVYGATNLADGVPSRFSG
SGSGAQYTLTISSLQPEDFATYYCQHFWGTPPYVFGGGTKLEIK

SEQ ID NO: 54
DIQMTQSPSSLSVSVGDRVTITCRASENIHSNLAWYQQKPGKAPQLLVYGATNLADGVPSRFSG
SGSGAQYTLTISSLQPEDFATYYCQHFWGTPPYVFGGGTKLEIK

SEQ ID NO: 55
EIVLTQSPATLSLSPGERATLSCSASSSVFDMYWYQQKPGQSPRPWIYRTSNLASGIPARFSGSGS
GTDFFLTISSLEPEDFAVYYCQQYQSFPLTFGQGTKLELK

SEQ ID NO: 56
EIVLTQSPATLSLSPGERVTLSCSASSSVFDMYWYQQKPGQSPRPWIYRTSNLASGIPARFSGSGS
GTDFFLTISSLEPEDAAVYYCQQYQSFPLTFGQGTKLELK

SEQ ID NO: 57
EIVLTQSPATLSLSPGERVTLSCSASSSVFDMYWYQQKPGSSPRPWIYRTSNLASGVPARFSGSGS
GTDFFLTISSLEPEDAAVYYCQQYQSFPLTFGQGTKLELK

-continued

SEQ ID NO: 58
EIVLTQSPATLSLSPGERVTLSCSASSSVFDMYWYQQKPGSSPRPWIYRTSNLASGVPARFSGSGS
GTDYFLTISSMEPEDAATYYCQQYQSFPLTFGQGTKLELK

SEQ ID NO: 59
DIQMTQSPSSLSASVGDRVTIICRASQEISGYLSWLQQKPDGTIKSLIYAASTLDPGVPSRFSGSRS
GADFTLTISSLQPEDFATYYCLQYAIYPPTFGQGTKLEIK

SEQ ID NO: 60
DIQMTQSPSSLSASVGDRVTLICRASQEISGYLSWLQQKPDGTIKRLIFAASTLDPGVPSRFSGSR
SGADFTLTISSLQPEDFADYYCLQYAIYPPTFGQGTKLEIK

SEQ ID NO: 61
DIQMTQSPSSLSASVGDRVTLICRASQEISGYLSWLQQKPDGTIKRLIFAASTLDPGVPSRFSGSR
SGADYTLTISSLQPEDFADYYCLQYAIYPPTFGQGTKLEIK

SEQ ID NO: 62
EIVLTQSPATLSLSPGERATLSCSASSSVSFMHWYQQKPGLAPRKLIYDTSKLASGIPDRFSGSGS
GTSYTLTISRLEPEDFAVYYCQQWTYYPPTFGQGTKVEIK

SEQ ID NO: 63
QIVLTQSPATLSLSPGERATLSCSASSSVSFMHWYQQKPGLAPRKWIYDTSKLASGVPDRFSGSG
SGTSYTLTISRLEPEDFAVYYCQQWTYYPPTFGQGTKVEIK

SEQ ID NO: 64
DIQMTQSPSSLSASVGDRVTITCRASQEISVYLSWLQQKPGKAPKRLIYAASTLDSGVPSRFSGSG
SGSDYTLTISSLQPEDFATYYCVQYTSHPYTFGQGTKVEIK

Humanized heavy chain variable domain

SEQ ID NO: 65
QVQLVQSGAEVVKPGASVKLSCKASGYTFTTFWMHWVRQAPGQGLEWIGNIYPGSGTINYDE
KFRSRVTLTVDTSISTAYMELSRLRSEDTAVYYCTTGWDGEHWGQGTTLTVSS

SEQ ID NO: 66
QVQLVQSGAEVVKPGASVKLSCKASGYTFTTFWMHWVRQAPGQGLEWIGNIYPGSGTINYDE
KFRSRATLTVDTSISTAYMEVSRLRSEDTAVYYCTTGWDGEHWGQGTTLTVSS

SEQ ID NO: 67
QVQLVQSGAEVVKPGASVKLSCKASGYTFTTFWMHWVKQAPGQGLEWIGNIYPGSGTINYDE
KFRSRATLTVDTSISTAYMEVSRLRSEDTAVYYCTTGWDGEHWGQGTTLTVSS

SEQ ID NO: 68
EVQLVESGGGLVKPGGSLRLSCAASGFTFSDYGMHWIRQAPGKGLEWVSYIGTTSSIIYYADTV
KGRFTISRDNAKNSLYLQMNSLRAEDTAVYYCARRDYGNYYWYLDVWGQGTMVTVSS

SEQ ID NO: 69
EVQLVESGGGLVKPGGSLRLSCAASGFTFSDYGMHWIRQAPGKGLEWIAYIGTTSSIIYYADTV
KGRFTISRDNAKNSLYLQMNSLRAEDTAVYYCARRDYGNYYWYLDVWGTGTMVTVSS

SEQ ID NO: 70
EVQLVESGGGLVKPGGSLRLSCAASGFTFSDYGMHWIRQAPGKGLEWIAYIGTTSSIIYYADTV
KGRFTISRDNAKNSLYLQMNSLRAEDTAMYYCARRDYGNYYWYLDVWGTGTMVTVSS

SEQ ID NO: 71
QVQLVQSGAEVKKPGASVKVSCKASGFNIKDTYMHWVQQAPGQRLEWMGRIDPMNGNSKYD
PKFQDRVTITADTSASTAYLELSSLRSEDTAVYYCTSSKWGDYWGQGTLLTVSS

SEQ ID NO: 72
QVQLVQSGAEVKKPGASVKVSCKASGFNIKDTYMHWVQQAPGQRLEWMGRIDPMNANSKYD
PKFQDRVTITADTSASTAYLELSSLRSEDTAVYYCTSSKWGDYWGQGTLLTVSS

SEQ ID NO: 73
QVQLVQSGAEVKKPGASVKLSCKASGFNIKDTYMHWVQQAPEQRLEWMGRIDPMNANSKYD
PKFQDRVTITADTSASTAYLELSSLRSEDTAVYYCTSSKWGDYWGQGTLLTVSS

-continued

SEQ ID NO: 74
QVQLVQSGAEVKKPGASVKLSCKASGFNIKDTYMHWVQQAPEQRLEWIGRIDPMNANSKYDP
KFQDRATITADTSANTAYLELSSLRSEDTAVYYCTSSKWGDYWGQGTLLTVSS

SEQ ID NO: 75
QVQLQQSGAEVKKPGASVKLSCTASGFNIKDTYMHWVQQAPEQRLEWIGRIDPMNGNSKYDP
KFQDRATITADTSANTAYLELSSLRSEDTAVYYCTSSKWGDYWGQGTLLTVSS

SEQ ID NO: 76
QVQLQQSGAEVKKPGASVKLSCTASGFNIKDTYMHWVQQAPEQRLEWIGRIDPMNANSKYDP
KFQDRATITADTSANTAYLELSSLRSEDTAVYYCTSSKWGDYWGQGTLLTVSS

SEQ ID NO: 77
QVQLVQSGAEVKKPGASVKVSCKASGYNIKDYYIHWVRQAPGQGLEWIDPDNGNTKYDP
NFQGRVTMTADTSTSTVYMELSSLRSEDTAVYYCARYGGYGGFYTMDYWGQGTLVTVSS

SEQ ID NO: 78
QVQLVQSGAEVKKPGASVKVSCKASGFNIKDYYIHWVRQAPGQGLEWIGWIDPDNGNTKYDP
NFQGRATMTADTSTSTVYMELSSLRSEDTAVYYCARYGGYGGFYTMDYWGQGTLVTVSS

SEQ ID NO: 79
QVQLVQSGAEVKKPGASVKVSCKASGYTFTIYWMHWVRQAPGQGLEWIGRIDPNSGDTKYTE
KFKNRATLTVDKSTSTAYMELSSLRSEDTAVYYCARGGPNWDGFAYWGQGTLVTVSS

SEQ ID NO: 80
QVQLVQSGAEVKKPGASVKVSCKASGYTFTIYWMHWVKQRPGQGLEWIGRIDPNSGDTKYTE
KFKNRATLTVDKSTSTAYMEFSSLRSEDTAVYYCARGGPNWDGFAYWGQGTLVTVSS

SEQ ID NO: 81
QVQLVQSGAEVVKPGASVKLSCKASGYTFTTFWMHWVRQAPGQGLEWIGNIYPGSGISNYDE
KFKNRVTLTVDTSISTAYMELSRLRSEDTAVYYCTTGWDGEHWGQGTTLTVSS

SEQ ID NO: 82
QVQLVQSGAEVVKPGASVKLSCKASGYTFTTFWMHWVRQAPGQGLEWIGNIYPGSGISNYDE
KFKNRATLTVDTSISTAYMEVSRLRSEDTAVYYCTTGWDGEHWGQGTTLTVSS

SEQ ID NO: 83
QVQLVQSGAEVVKPGASVKLSCKASGYTFTTFWMHWVKQAPGQGLEWIGNIYPGSGISNYDE
KFKNRATLTVDTSISTAYMEVSRLRSEDTAVYYCTTGWDGEHWGQGTTLTVSS

Humanized light chains

SEQ ID NO: 84
DIQMTQSPSSLSASVGDRVTITCRASENIHSNLAWYQQKPGKAPKLLVYGATNLADGVPSRFSG
SGSGAQYTLTISSLQPEDFATYYCQHFWGTPPYAFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 85
DIQMTQSPSSLSASVGDRVTITCRASENIHSNLAWYQQKPGKAPQLLVYGATNLADGVPSRFSG
SGSGAQYTLTISSLQPEDFATYYCQHFWGTPPYAFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 86
DIQMTQSPSSLSVSVGDRVTITCRASENIHSNLAWYQQKPGKAPQLLVYGATNLADGVPSRFSG
SGSGAQYTLTISSLQPEDFATYYCQHFWGTPPYAFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 87
DIQMTQSPSSLSASVGDRVTITCRASENIHSNLAWYQQKPGKAPKLLVYGATNLADGVPSRFSG
SGSGAQYTLTISSLQPEDFATYYCQHFWGTPPYVFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 88
DIQMTQSPSSLSASVGDRVTITCRASENIHSNLAWYQQKPGKAPQLLVYGATNLADGVPSRFSG
SGSGAQYTLTISSLQPEDFATYYCQHFWGTPPYVFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 89
DIQMTQSPSSLSVSVGDRVTITCRASENIHSNLAWYQQKPGKAPQLLVYGATNLADGVPSRFSG
SGSGAQYTLTISSLQPEDFATYYCQHFWGTPPYVFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC

SEQ ID NO: 90
EIVLTQSPATLSLSPGERATLSCSASSSVEDMYWYQQKPGQSPRPWIYRTSNLASGIPARFSGSGS
GTDFFLTISSLEPEDFAVYYCQQYQSFPLTFGQGTKLELKRTVAAPSVFIFPPSDEQLKSGTASVV
CLLNNFYPREAKVQWKVDNALQSGNSQESVTEQDSKDSTYSLSSTLTLSKADYEKHKVYACEV
THQGLSSPVTKSFNRGEC

SEQ ID NO: 91
EIVLTQSPATLSLSPGERVTLSCSASSSVEDMYWYQQKPGQSPRPWIYRTSNLASGIPARFSGSGS
GTDFFLTISSLEPEDAAVYYCQQYQSFPLTFGQGTKLELKRTVAAPSVFIFPPSDEQLKSGTASVV
CLLNNFYPREAKVQWKVDNALQSGNSQESVTEQDSKDSTYSLSSTLTLSKADYEKHKVYACEV
THQGLSSPVTKSFNRGEC

SEQ ID NO: 92
EIVLTQSPATLSLSPGERVTLSCSASSSVFDMYWYQQKPGSSPRPWIYRTSNLASGVPARFSGSGS
GTDFFLTISSLEPEDAAVYYCQQYQSFPLTFGQGTKLELKRTVAAPSVFIFPPSDEQLKSGTASVV
CLLNNFYPREAKVQWKVDNALQSGNSQESVTEQDSKDSTYSLSSTLTLSKADYEKHKVYACEV
THQGLSSPVTKSFNRGEC

SEQ ID NO: 93
EIVLTQSPATLSLSPGERVTLSCSASSSVFDMYWYQQKPGSSPRPWIYRTSNLASGVPARFSGSGS
GTDYFLTISSMEPEDAATYYCQQYQSFPLTFGQGTKLELKRTVAAPSVFIFPPSDEQLKSGTASV
VCLLNNFYPREAKVQWKVDNALQSGNSQESVTEQDSKDSTYSLSSTLTLSKADYEKHKVYACE
VTHQGLSSPVTKSFNRGEC

SEQ ID NO: 94
DIQMTQSPSSLSASVGDRVTIICRASQEISGYLSWLQQKPDGTIKSLIYAASTLDPGVPSRFSGSRS
GADFTLTISSLQPEDFATYYCLQYAIYPPTFGQGTKLEIKRTVAAPSVFIFPPSDEQLKSGTASVVC
LLNNFYPREAKVQWKVDNALQSGNSQESVTEQDSKDSTYSLSSTLTLSKADYEKHKVYACEVT
HQGLSSPVTKSFNRGEC

SEQ ID NO: 95
DIQMTQSPSSLSASVGDRVTLICRASQEISGYLSWLQQKPDGTIKRLIFAASTLDPGVPSRFSGSR
SGADFTLTISSLQPEDFADYYCLQYAIYPPTFGQGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEV
THQGLSSPVTKSFNRGEC

SEQ ID NO: 96
DIQMTQSPSSLSASVGDRVTLICRASQEISGYLSWLQQKPDGTIKRLIFAASTLDPGVPSRFSGSR

SGADYTLTISSLQPEDFADYYCLQYAIYPPTFGQGTKLEIKRTVAAPSVFIFPPSDEQLKSGTASV

VCLLNNFYPREAKVQWKVDNALQSGNSQESVTEQDSKDSTYSLSSTLTLSKADYEKHKVYACE

VTHQGLSSPVTKSFNRGEC

SEQ ID NO: 97
EIVLTQSPATLSLSPGERATLSCSASSSVSFMHWYQQKPGLAPRKLIYDTSKLASGIPDRFSGSGS

GTSYTLTISRLEPEDFAVYYCQQWTYYPPTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACE

VTHQGLSSPVTKSFNRGEC

SEQ ID NO: 98
QIVLTQSPATLSLSPGERATLSCSASSSVSFMHWYQQKPGLAPRKWIYDTSKLASGVPDRFSGSG

SGTSYTLTISRLEPEDFAVYYCQQWTYYPPTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACE

VTHQGLSSPVTKSFNRGEC

SEQ ID NO: 99
DIQMTQSPSSLSASVGDRVTITCRASQEISVYLSWLQQKPGKAPKRLIYAASTLDSGVPSRFSGSG

SGSDYTLTISSLQPEDFATYYCVQYTSHPYTFGQGTKVEIKRTVAAPSVFIFPPSDEQLKSGTASV

VCLLNNFYPREAKVQWKVDNALQSGNSQESVTEQDSKDSTYSLSSTLTLSKADYEKHKVYACE

VTHQGLSSPVTKSFNRGEC

Humanized heavy chains
SEQ ID NO: 100
QVQLVQSGAEVVKPGASVKLSCKASGYTFTTFWMHWVRQAPGQGLEWIGNIYPGSGTINYDE

KFRSRVTLTVDTSISTAYMELSRLRSEDTAVYYCTTGWDGEHWGQGTTLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 101
QVQLVQSGAEVVKPGASVKLSCKASGYTFTTFWMHWVRQAPGQGLEWIGNIYPGSGTINYDE

KFRSRATLTVDTSISTAYMEVSRLRSEDTAVYYCTTGWDGEHWGQGTTLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 102
QVQLVQSGAEVVKPGASVKLSCKASGYTFTTFWMHWVKQAPGQGLEWIGNIYPGSGTINYDE

KFRSRATLTVDTSISTAYMEVSRLRSEDTAVYYCTTGWDGEHWGQGTTLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 103
EVQLVESGGGLVKPGGSLRLSCAASGFTFSDYGMHWIRQAPGKGLEWVSYIGTTSSIIYYADTV

KGRFTISRDNAKNSLYLQMNSLRAEDTAVYYCARRDYGNYYWYLDVWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSL

SPGK

SEQ ID NO: 104
EVQLVESGGGLVKPGGSLRLSCAASGFTFSDYGMHWIRQAPGKGLEWIAYIGTTSSIIYYADTV

KGRFTISRDNAKNSLYLQMNSLRAEDTAVYYCARRDYGNYYWYLDVWGTGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSL

SPGK

SEQ ID NO: 105
EVQLVESGGGLVKPGGSLRLSCAASGFTFSDYGMHWIRQAPGKGLEWIAYIGTTSSIIYYADTV

KGRFTISRDNAKNSLYLQMNSLRAEDTAMYYCARRDYGNYYWYLDVWGTGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSL

SPGK

SEQ ID NO: 106
QVQLVQSGAEVKKPGASVKVSCKASGFNIKDTYMHWVQQAPGQRLEWMGRIDPMNGNSKYD

PKFQDRVTITADTSASTAYLELSSLRSEDTAVYYCTSSKWGDYWGQGTLLTVSSASTKGPSVFP

LAPSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 107
QVQLVQSGAEVKKPGASVKVSCKASGFNIKDTYMHWVQQAPGQRLEWMGRIDPMNANSKYD

PKFQDRVTITADTSASTAYLELSSLRSEDTAVYYCTSSKWGDYWGQGTLLTVSSASTKGPSVFP

LAPSSKSTSGGTAALGCLVKDYFPEPVTVSWNSGALTSGVHTFPAVLQSSGLYSLSSVVTVPS SL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 108

QVQLVQSGAEVKKPGASVKLSCKASGFNIKDTYMHWVQQAPEQRLEWMGRIDPMNANSKYD

PKFQDRVTITADTSASTAYLELSSLRSEDTAVYYCTSSKWGDYWGQGTLLTVSSASTKGPSVFP

LAPSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 109

QVQLVQSGAEVKKPGASVKLSCKASGFNIKDTYMHWVQQAPEQRLEWIGRIDPMNANSKYDP

KFQDRATITADTSANTAYLELSSLRSEDTAVYYCTSSKWGDYWGQGTLLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 110

QVQLQQSGAEVKKPGASVKLSCTASGFNIKDTYMHWVQQAPEQRLEWIGRIDPMNGNSKYDP

KFQDRATITADTSANTAYLELSSLRSEDTAVYYCTSSKWGDYWGQGTLLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 111

QVQLQQSGAEVKKPGASVKLSCTASGFNIKDTYMHWVQQAPEQRLEWIGRIDPMNANSKYDP

KFQDRATITADTSANTAYLELSSLRSEDTAVYYCTSSKWGDYWGQGTLLTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 112

QVQLVQSGAEVKKPGASVKVSCKASGYNIKDYYIHWVRQAPGQGLEWIGWIDPDNGNTKYDP

NFQGRVTMTADTSTSTVYMELSSLRSEDTAVYYCARYGGYGGFYTMDYWGQGTLVTVSSAST

KGPSVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSL

SLSPGK

SEQ ID NO: 113

QVQLVQSGAEVKKPGASVKVSCKASGFNIKDYYIHWVRQAPGQGLEWIGWIDPDNGNTKYDP
NFQGRATMTADTSTSTVYMELSSLRSEDTAVYYCARYGGYGGFYTMDYWGQGTLVTVSSAST
KGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSL
SLSPGK

SEQ ID NO: 114

QVQLVQSGAEVKKPGASVKVSCKASGYTFTIYWMHWVRQAPGQGLEWIGRIDPNSGDTKYTE
KFKNRATLTVDKSTSTAYMELSSLRSEDTAVYYCARGGPNWDGFAYWGQGTLVTVSSASTKG
PSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSL
SPGK

SEQ ID NO: 115

QVQLVQSGAEVKKPGASVKVSCKASGYTFTIYWMHWVKQRPGQGLEWIGRIDPNSGDTKYTE
KFKNRATLTVDKSTSTAYMEFSSLRSEDTAVYYCARGGPNWDGFAYWGQGTLVTVSSASTKG
PSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSL
SPGK

SEQ ID NO: 116

QVQLVQSGAEVVKPGASVKLSCKASGYTFTTFWMHWVRQAPGQGLEWIGNIYPGSGISNYDE
KFKNRVTLTVDTSISTAYMELSRLRSEDTAVYYCTTGWDGEHWGQGTTLTVSSASTKGPSVFP
LAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

SEQ ID NO: 117

QVQLVQSGAEVVKPGASVKLSCKASGYTFTTFWMHWVRQAPGQGLEWIGNIYPGSGISNYDE
KFKNRATLTVDTSISTAYMEVSRLRSEDTAVYYCTTGWDGEHWGQGTTLTVSSASTKGPSVFP
LAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

SEQ ID NO: 118

QVQLVQSGAEVVKPGASVKLSCKASGYTFTTFWMHWVKQAPGQGLEWIGNIYPGSGISNYDE
KFKNRATLTVDTSISTAYMEVSRLRSEDTAVYYCTTGWDGEHWGQGTTLTVSSASTKGPSVFP
LAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

---

What is claimed is:

1. A monoclonal antibody, or an antigen-binding portion thereof, comprising
   a heavy chain variable region CDR1 comprising SEQ ID NO:31;
   a heavy chain variable region CDR2 comprising SEQ ID NO:37;
   a heavy chain variable region CDR3 comprising SEQ ID NO:43;
   a light chain variable region CDR1 comprising SEQ ID NO:13;
   a light chain variable region CDR2 comprising SEQ ID NO:19; and
   a light chain variable region CDR3 comprising SEQ ID NO:25;
   wherein said antibody or portion specifically binds to human PD-L1.

2. A monoclonal antibody, or an antigen-binding portion thereof, comprising:
   a heavy chain variable region CDR1 comprising SEQ ID NO:32;
   a heavy chain variable region CDR2 comprising SEQ ID NO:38;
   a heavy chain variable region CDR3 comprising SEQ ID NO:44;
   a light chain variable region CDR1 comprising SEQ ID NO:14;
   a light chain variable region CDR2 comprising SEQ ID NO:20; and
   a light chain variable region CDR3 comprising SEQ ID NO:26;
   wherein said antibody or portion specifically binds to human PD-L1.

3. A monoclonal antibody, or an antigen-binding portion thereof, comprising:
   a heavy chain variable region CDR1 comprising SEQ ID NO:33;
   a heavy chain variable region CDR2 comprising SEQ ID NO:39;
   a heavy chain variable region CDR3 comprising SEQ ID NO:45;
   a light chain variable region CDR1 comprising SEQ ID NO:15;
   a light chain variable region CDR2 comprising SEQ ID NO:21; and
   a light chain variable region CDR3 comprising SEQ ID NO:27;
   wherein said antibody or portion specifically binds to human PD-L1.

4. The monoclonal antibody, or antigen-binding portion thereof, of claim 1, which comprises a light chain variable region amino acid sequence having at least 95% identity to SEQ ID NO:1 and a heavy chain variable region amino acid sequence having at least 95% identity to SEQ ID NO:7.

5. The monoclonal antibody, or an antigen-binding portion thereof, of claim 1, which comprises a heavy chain variable region comprising an amino acid sequence that has at least 95%, at least 96%, at least 97%, at least 98%, or at least 99% identical to a sequence as set forth in SEQ ID NO:7.

6. The monoclonal antibody, or antigen-binding portion thereof, of claim 2, which comprises a light chain variable region amino acid sequence having at least 95% identity to SEQ ID NO:2 and a heavy chain variable region amino acid sequence having at least 95% identity to SEQ ID NO:8.

7. The monoclonal antibody, or an antigen-binding portion thereof, of 2, which comprises a heavy chain variable region comprising an amino acid sequence that has at least 95%, at least 96%, at least 97%, at least 98%, or at least 99% identical to a sequence as set forth in SEQ ID NO:8.

8. The monoclonal antibody, or antigen-binding portion thereof, of claim 3, which comprises a light chain variable region amino acid sequence having at least 95% identity to SEQ ID NO:3 and a heavy chain variable region amino acid sequence having at least 95% identity to SEQ ID NO:9.

9. The monoclonal antibody, or an antigen-binding portion thereof, of claim 3, which comprises a heavy chain variable region comprising an amino acid sequence that has at least 95%, at least 96%, at least 97%, at least 98%, or at least 99% identical to a sequence as set forth in SEQ ID NO:9.

10. A monoclonal antibody, or antigen-binding portion thereof, comprising: a heavy chain variable region comprising an amino acid sequence selected from the group consisting of SEQ ID NOs: 65-67 and a light chain variable region comprising an amino acid sequence selected from the group consisting of SEQ ID NOs: 49-51.

11. A monoclonal antibody, or antigen-binding portion thereof, comprising: a heavy chain variable region comprising an amino acid sequence selected from the group consisting of SEQ ID NOs: 68-70 and a light chain variable region comprising an amino acid sequence selected from the group consisting of SEQ ID NOs: 55-58.

12. A monoclonal antibody, or antigen-binding portion thereof, comprising: a heavy chain variable region comprising an amino acid sequence selected from the group consisting of SEQ ID NOs: 71-76 and a light chain variable region comprising an amino acid sequence selected from the group consisting of SEQ ID NOs: 59-61.

13. The monoclonal antibody, or antigen-binding portion thereof, of claim 1, which is a Fab fragment, an F(ab')$_2$ fragment, an Fv fragment, a single chain antibody, or a bispecific antibody.

14. The monoclonal antibody of claim 1, which is an immunoglobulin G (IgG), an IgM, an IgE, an IgA or an IgD molecule.

15. The monoclonal antibody, or antigen-binding portion thereof, of claim 2, which is a Fab fragment, an F(ab')$_2$ fragment, an Fv fragment, a single chain antibody, or a bispecific antibody.

16. The monoclonal antibody of claim 2, which is an immunoglobulin G (IgG), an IgM, an IgE, an IgA or an IgD molecule.

17. The monoclonal antibody, or antigen-binding portion thereof, of claim 3, which is a Fab fragment, an F(ab')$_2$ fragment, an Fv fragment, a single chain antibody, or a bispecific antibody.

18. The monoclonal antibody of claim 3, which is an immunoglobulin G (IgG), an IgM, an IgE, an IgA or an IgD molecule.

* * * * *

SEQUENCE LISTING

<160> NUMBER OF SEQ ID NOS: 118

<210> SEQ ID NO 1
<211> LENGTH: 108
<212> TYPE: PRT
<213> ORGANISM: Mus musculus

<400> SEQUENCE: 1

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile His Ser Asn
                20                  25                  30

Leu Ala Trp Tyr Gln Gln Lys Gln Gly Lys Ser Pro Gln Leu Leu Val
            35                  40                  45

Tyr Gly Ala Thr Asn Leu Ala Asp Gly Val Pro Ser Arg Phe Ser Gly
    50                  55                  60

Ser Gly Ser Gly Ala Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Tyr Ala Phe Gly Gly Gly Thr Lys Leu Glu Thr Lys
            100                 105
```

<210> SEQ ID NO 2
<211> LENGTH: 106
<212> TYPE: PRT
<213> ORGANISM: Mus musculus

<400> SEQUENCE: 2

```
Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Phe Asp Met
                20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
    50                  55                  60

Gly Ser Gly Thr Ser Tyr Phe Leu Thr Ile Ser Ser Met Glu Ala Glu
65                  70                  75                  80

Asp Ala Ala Thr Tyr Tyr Cys Gln Gln Tyr Gln Ser Phe Pro Leu Thr
                85                  90                  95

Phe Gly Ala Gly Thr Lys Leu Glu Leu Lys
            100                 105
```

<210> SEQ ID NO 3
<211> LENGTH: 107
<212> TYPE: PRT
<213> ORGANISM: Mus musculus

<400> SEQUENCE: 3

Asp Ile Gln Met Thr Gln Ser Pro Ser Ser Leu Ser Ala Ser Leu Gly
1               5                   10                  15

Glu Arg Val Ser Leu Ile Cys Arg Ala Ser Gln Glu Ile Ser Gly Tyr
            20                  25                  30

Leu Ser Trp Leu Gln Gln Lys Ser Asp Gly Thr Ile Lys Arg Leu Ile
        35                  40                  45

Phe Ala Ala Ser Thr Leu Asp Pro Gly Val Pro Lys Arg Phe Ser Gly
    50                  55                  60

Ser Arg Ser Gly Ala Asp Tyr Ser Leu Thr Ile Ser Ser Leu Glu Ser
65                  70                  75                  80

Glu Asp Phe Ala Asp Tyr Tyr Cys Leu Gln Tyr Ala Ile Tyr Pro Pro
                85                  90                  95

Thr Phe Gly Ser Gly Thr Lys Leu Glu Ile Lys
            100                 105

<210> SEQ ID NO 4
<211> LENGTH: 106
<212> TYPE: PRT
<213> ORGANISM: Mus musculus

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Phe Met
            20                  25                  30

His Trp Tyr Gln Gln Lys Ser Gly Thr Ser Pro Lys Lys Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ile Asn Met Glu Ala Glu
65                  70                  75                  80

Asp Ala Ala Thr Tyr Tyr Cys Gln Gln Trp Thr Tyr Tyr Pro Pro Thr
                85                  90                  95

Phe Gly Gly Gly Thr Lys Leu Glu Ile Lys
            100                 105

<210> SEQ ID NO 5
<211> LENGTH: 107
<212> TYPE: PRT
<213> ORGANISM: Mus musculus

<400> SEQUENCE: 5

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Gln Arg Phe Arg Gly
    50                  55                  60

Ser Arg Ser Gly Ser Asp Tyr Ser Leu Thr Ile Ser Ser Leu Glu Ser

```
                65                  70                  75                  80
Glu Asp Phe Ala Asp Tyr Tyr Cys Val Gln Tyr Thr Ser His Pro Tyr
                    85                  90                  95

Thr Phe Gly Gly Gly Thr Lys Leu Glu Ile Lys
                100                 105

<210> SEQ ID NO 6
<211> LENGTH: 108
<212> TYPE: PRT
<213> ORGANISM: Mus musculus

<400> SEQUENCE: 6

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile His Ser Asn
            20                  25                  30

Leu Ala Trp Tyr Gln Gln Lys Gln Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Tyr Val Phe Gly Gly Gly Thr Lys Leu Glu Thr Lys
                100                 105

<210> SEQ ID NO 7
<211> LENGTH: 115
<212> TYPE: PRT
<213> ORGANISM: Mus musculus

<400> SEQUENCE: 7

Gln Val Gln Leu Gln Pro Gly Ser Glu Leu Val Arg Pro Gly Thr
1               5                   10                  15

Ser Val Lys Leu Ser Cys Lys Ala Ser Gly Tyr Thr Phe Thr Thr Phe
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Thr Ile Asn Tyr Asp Glu Lys Phe
    50                  55                  60

Arg Ser Lys Ala Thr Leu Thr Val Asp Thr Ser Ser Asn Thr Ala Tyr
65                  70                  75                  80

Met Gln Val Ser Ser Leu Thr Ser Glu Asp Ser Ala Val Tyr Tyr Cys
                85                  90                  95

Thr Thr Gly Trp Asp Gly Glu His Trp Gly Gln Gly Thr Thr Leu Thr
                100                 105                 110

Val Ser Ser
        115

<210> SEQ ID NO 8
<211> LENGTH: 121
<212> TYPE: PRT
<213> ORGANISM: Mus musculus

<400> SEQUENCE: 8

Glu Val Gln Leu Val Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Asp Tyr
            20                  25                  30

Gly Met His Trp Ile Arg Gln Ala Pro Glu Lys Gly Leu Glu Trp Ile
            35                  40                  45

Ala Tyr Ile Gly Thr Thr Ser Ser Ile Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Asp Tyr Gly Asn Tyr Tyr Trp Tyr Leu Asp Val Trp Gly
            100                 105                 110

Thr Gly Thr Thr Val Thr Val Ser Ser
            115                 120

<210> SEQ ID NO 9
<211> LENGTH: 115
<212> TYPE: PRT
<213> ORGANISM: Mus musculus

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Gln Gln Arg Pro Glu Gln Gly Leu Glu Trp Ile
            35                  40                  45

Gly Arg Ile Asp Pro Met Asn Gly Asn Ser Lys Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ser Ser Lys Trp Gly Asp Tyr Trp Gly Gln Gly Thr Thr Leu Thr
            100                 105                 110

Val Ser Ser
        115

<210> SEQ ID NO 10
<211> LENGTH: 121
<212> TYPE: PRT
<213> ORGANISM: Mus musculus

<400> SEQUENCE: 10

Glu Val Gln Leu Gln Gln Ser Gly Ala Glu Leu Val Arg Pro Gly Ala
1               5                   10                  15

Leu Val Lys Val Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
            35                  40                  45

Gly Trp Ile Asp Pro Asp Asn Gly Asn Thr Lys Tyr Asp Pro Asn Phe
    50                  55                  60

Gln Gly Lys Ala Ser Met Thr Ala Asp Thr Ser Ser Asn Thr Val Asn
65                  70                  75                  80

Leu Gln Leu Ser Ser Leu Thr Ser Lys Asp Thr Ala Val Tyr Tyr Cys
                85                  90                  95
```

```
Ala Arg Tyr Gly Gly Tyr Gly Phe Tyr Thr Met Asp Tyr Trp Gly
                100                 105                 110

Gln Gly Thr Ser Val Thr Val Ser Ser
        115                 120
```

<210> SEQ ID NO 11
<211> LENGTH: 119
<212> TYPE: PRT
<213> ORGANISM: Mus musculus

<400> SEQUENCE: 11

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ile Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Asp Thr Lys Tyr Thr Glu Lys Phe
    50                  55                  60

Lys Asn Arg Ala Thr Leu Thr Val Asp Lys Ser Ser Asn Thr Ala Tyr
65                  70                  75                  80

Met Gln Phe Ser Ser Leu Ala Ser Asp Asp Ser Ala Val Tyr Tyr Cys
                85                  90                  95

Ala Arg Gly Gly Pro Asn Trp Asp Gly Phe Ala Tyr Trp Gly Gln Gly
                100                 105                 110

Thr Leu Val Thr Val Ser Ala
        115
```

<210> SEQ ID NO 12
<211> LENGTH: 115
<212> TYPE: PRT
<213> ORGANISM: Mus musculus

<400> SEQUENCE: 12

```
Gln Val Gln Leu Gln Gln Pro Arg Ser Glu Leu Val Arg Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Lys Gln Arg Pro Gly Gln Gly Leu Glu Trp Ile
        35                  40                  45

Gly Asn Ile Tyr Pro Gly Ser Gly Ile Ser Asn Tyr Asp Glu Lys Phe
    50                  55                  60

Lys Asn Lys Ala Thr Leu Thr Val Asp Thr Ser Ser Ser Thr Ala Tyr
65                  70                  75                  80

Met Gln Val Ser Ser Leu Thr Ser Glu Asp Ser Ala Val Tyr Tyr Cys
                85                  90                  95

Thr Thr Gly Trp Asp Gly Glu His Trp Gly Gln Gly Thr Thr Leu Thr
                100                 105                 110

Val Ser Ser
    115
```

<210> SEQ ID NO 13
<211> LENGTH: 11
<212> TYPE: PRT
<213> ORGANISM: Mus musculus

<400> SEQUENCE: 13

Arg Ala Ser Glu Asn Ile His Ser Asn Leu Ala
1               5                   10

<210> SEQ ID NO 14
<211> LENGTH: 10
<212> TYPE: PRT
<213> ORGANISM: Mus musculus

<400> SEQUENCE: 14

Ser Ala Ser Ser Ser Val Phe Asp Met Tyr
1               5                   10

<210> SEQ ID NO 15
<211> LENGTH: 11
<212> TYPE: PRT
<213> ORGANISM: Mus musculus

<400> SEQUENCE: 15

Arg Ala Ser Gln Glu Ile Ser Gly Tyr Leu Ser
1               5                   10

<210> SEQ ID NO 16
<211> LENGTH: 10
<212> TYPE: PRT
<213> ORGANISM: Mus musculus

<400> SEQUENCE: 16

Ser Ala Ser Ser Ser Val Ser Phe Met His
1               5                   10

<210> SEQ ID NO 17
<211> LENGTH: 11
<212> TYPE: PRT
<213> ORGANISM: Mus musculus

<400> SEQUENCE: 17

Arg Ala Ser Gln Glu Ile Ser Val Tyr Leu Ser
1               5                   10

<210> SEQ ID NO 18
<211> LENGTH: 11
<212> TYPE: PRT
<213> ORGANISM: Mus musculus

<400> SEQUENCE: 18

Arg Ala Ser Glu Asn Ile His Ser Asn Leu Ala
1               5                   10

<210> SEQ ID NO 19
<211> LENGTH: 7
<212> TYPE: PRT
<213> ORGANISM: Mus musculus

<400> SEQUENCE: 19

Gly Ala Thr Asn Leu Ala Asp
1               5

<210> SEQ ID NO 20
<211> LENGTH: 7
<212> TYPE: PRT
<213> ORGANISM: Mus musculus

<400> SEQUENCE: 20

Arg Thr Ser Asn Leu Ala Ser
1               5

```
<210> SEQ ID NO 21
<211> LENGTH: 7
<212> TYPE: PRT
<213> ORGANISM: Mus musculus

<400> SEQUENCE: 21

Ala Ala Ser Thr Leu Asp Pro
1               5

<210> SEQ ID NO 22
<211> LENGTH: 7
<212> TYPE: PRT
<213> ORGANISM: Mus musculus

<400> SEQUENCE: 22

Asp Thr Ser Lys Leu Ala Ser
1               5

<210> SEQ ID NO 23
<211> LENGTH: 7
<212> TYPE: PRT
<213> ORGANISM: Mus musculus

<400> SEQUENCE: 23

Ala Ala Ser Thr Leu Asp Ser
1               5

<210> SEQ ID NO 24
<211> LENGTH: 7
<212> TYPE: PRT
<213> ORGANISM: Mus musculus

<400> SEQUENCE: 24

Gly Ala Thr Asn Leu Ala Asp
1               5

<210> SEQ ID NO 25
<211> LENGTH: 10
<212> TYPE: PRT
<213> ORGANISM: Mus musculus

<400> SEQUENCE: 25

Gln His Phe Trp Gly Thr Pro Pro Tyr Ala
1               5                   10

<210> SEQ ID NO 26
<211> LENGTH: 9
<212> TYPE: PRT
<213> ORGANISM: Mus musculus

<400> SEQUENCE: 26

Gln Gln Tyr Gln Ser Phe Pro Leu Thr
1               5

<210> SEQ ID NO 27
<211> LENGTH: 9
<212> TYPE: PRT
<213> ORGANISM: Mus musculus

<400> SEQUENCE: 27

Leu Gln Tyr Ala Ile Tyr Pro Pro Thr
1               5
```

```
<210> SEQ ID NO 28
<211> LENGTH: 9
<212> TYPE: PRT
<213> ORGANISM: Mus musculus

<400> SEQUENCE: 28

Gln Gln Trp Thr Tyr Tyr Pro Pro Thr
1               5

<210> SEQ ID NO 29
<211> LENGTH: 9
<212> TYPE: PRT
<213> ORGANISM: Mus musculus

<400> SEQUENCE: 29

Val Gln Tyr Thr Ser His Pro Tyr Thr
1               5

<210> SEQ ID NO 30
<211> LENGTH: 10
<212> TYPE: PRT
<213> ORGANISM: Mus musculus

<400> SEQUENCE: 30

Gln His Phe Trp Gly Thr Pro Pro Tyr Val
1               5                   10

<210> SEQ ID NO 31
<211> LENGTH: 5
<212> TYPE: PRT
<213> ORGANISM: Mus musculus

<400> SEQUENCE: 31

Thr Phe Trp Met His
1               5

<210> SEQ ID NO 32
<211> LENGTH: 5
<212> TYPE: PRT
<213> ORGANISM: Mus musculus

<400> SEQUENCE: 32

Asp Tyr Gly Met His
1               5

<210> SEQ ID NO 33
<211> LENGTH: 5
<212> TYPE: PRT
<213> ORGANISM: Mus musculus

<400> SEQUENCE: 33

Asp Thr Tyr Met His
1               5

<210> SEQ ID NO 34
<211> LENGTH: 5
<212> TYPE: PRT
<213> ORGANISM: Mus musculus

<400> SEQUENCE: 34

Asp Tyr Tyr Ile His
1               5

<210> SEQ ID NO 35
<211> LENGTH: 5
```

```
<212> TYPE: PRT
<213> ORGANISM: Mus musculus

<400> SEQUENCE: 35

Ile Tyr Trp Met His
1               5

<210> SEQ ID NO 36
<211> LENGTH: 5
<212> TYPE: PRT
<213> ORGANISM: Mus musculus

<400> SEQUENCE: 36

Thr Phe Trp Met His
1               5

<210> SEQ ID NO 37
<211> LENGTH: 17
<212> TYPE: PRT
<213> ORGANISM: Mus musculus

<400> SEQUENCE: 37

Asn Ile Tyr Pro Gly Ser Gly Thr Ile Asn Tyr Asp Glu Lys Phe Arg
1               5                   10                  15

Ser

<210> SEQ ID NO 38
<211> LENGTH: 17
<212> TYPE: PRT
<213> ORGANISM: Mus musculus

<400> SEQUENCE: 38

Tyr Ile Gly Thr Thr Ser Ser Ile Ile Tyr Tyr Ala Asp Thr Val Lys
1               5                   10                  15

Gly

<210> SEQ ID NO 39
<211> LENGTH: 17
<212> TYPE: PRT
<213> ORGANISM: Mus musculus

<400> SEQUENCE: 39

Arg Ile Asp Pro Met Asn Gly Asn Ser Lys Tyr Asp Pro Lys Phe Gln
1               5                   10                  15

Asp

<210> SEQ ID NO 40
<211> LENGTH: 17
<212> TYPE: PRT
<213> ORGANISM: Mus musculus

<400> SEQUENCE: 40

Trp Ile Asp Pro Asp Asn Gly Asn Thr Lys Tyr Asp Pro Asn Phe Gln
1               5                   10                  15

Gly

<210> SEQ ID NO 41
<211> LENGTH: 17
<212> TYPE: PRT
<213> ORGANISM: Mus musculus

<400> SEQUENCE: 41
```

Arg Ile Asp Pro Asn Ser Gly Asp Thr Lys Tyr Thr Glu Lys Phe Lys
1               5                   10                  15

Asn

<210> SEQ ID NO 42
<211> LENGTH: 17
<212> TYPE: PRT
<213> ORGANISM: Mus musculus

<400> SEQUENCE: 42

Asn Ile Tyr Pro Gly Ser Gly Ile Ser Asn Tyr Asp Glu Lys Phe Lys
1               5                   10                  15

Asn

<210> SEQ ID NO 43
<211> LENGTH: 6
<212> TYPE: PRT
<213> ORGANISM: Mus musculus

<400> SEQUENCE: 43

Gly Trp Asp Gly Glu His
1               5

<210> SEQ ID NO 44
<211> LENGTH: 12
<212> TYPE: PRT
<213> ORGANISM: Mus musculus

<400> SEQUENCE: 44

Arg Asp Tyr Gly Asn Tyr Tyr Trp Tyr Leu Asp Val
1               5                   10

<210> SEQ ID NO 45
<211> LENGTH: 6
<212> TYPE: PRT
<213> ORGANISM: Mus musculus

<400> SEQUENCE: 45

Ser Lys Trp Gly Asp Tyr
1               5

<210> SEQ ID NO 46
<211> LENGTH: 12
<212> TYPE: PRT
<213> ORGANISM: Mus musculus

<400> SEQUENCE: 46

Tyr Gly Gly Tyr Gly Gly Phe Tyr Thr Met Asp Tyr
1               5                   10

<210> SEQ ID NO 47
<211> LENGTH: 10
<212> TYPE: PRT
<213> ORGANISM: Mus musculus

<400> SEQUENCE: 47

Gly Gly Pro Asn Trp Asp Gly Phe Ala Tyr
1               5                   10

<210> SEQ ID NO 48
<211> LENGTH: 6
<212> TYPE: PRT
<213> ORGANISM: Mus musculus

```
<400> SEQUENCE: 48

Gly Trp Asp Gly Glu His
1               5

<210> SEQ ID NO 49
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys
            100                 105

<210> SEQ ID NO 50
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys
            100                 105

<210> SEQ ID NO 51
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 51

Asp Ile Gln Met Thr Gln Ser Pro Ser Ser Leu Ser Val Ser Val Gly
1               5                   10                  15
```

```
Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys
            100                 105
```

<210> SEQ ID NO 52
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Val Phe Gly Gly Gly Thr Lys Leu Glu Ile Lys
            100                 105
```

<210> SEQ ID NO 53
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Val Phe Gly Gly Gly Thr Lys Leu Glu Ile Lys
```

<210> SEQ ID NO 54
<211> LENGTH: 108
<212> TYPE: PRT
<213> ORGANISM: Artificial Sequence
<220> FEATURE:
<223> OTHER INFORMATION: Humanized light chain variable domain

<400> SEQUENCE: 54

Asp Ile Gln Met Thr Gln Ser Pro Ser Ser Leu Ser Val Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Val Phe Gly Gly Gly Thr Lys Leu Glu Ile Lys
            100                 105

<210> SEQ ID NO 55
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Phe Asp Met
            20                  25                  30

Tyr Trp Tyr Gln Gln Lys Pro Gly Gln Ser Pro Arg Pro Trp Ile Tyr
        35                  40                  45

Arg Thr Ser Asn Leu Ala Ser Gly Ile Pro Ala Arg Phe Ser Gly Ser
    50                  55                  60

Gly Ser Gly Thr Asp Phe Phe Leu Thr Ile Ser Ser Leu Glu Pro Glu
65                  70                  75                  80

Asp Phe Ala Val Tyr Tyr Cys Gln Gln Tyr Gln Ser Phe Pro Leu Thr
                85                  90                  95

Phe Gly Gln Gly Thr Lys Leu Glu Leu Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 56

Glu Ile Val Leu Thr Gln Ser Pro Ala Thr Leu Ser Leu Ser Pro Gly
1               5                   10                  15

Glu Arg Val Thr Leu Ser Cys Ser Ala Ser Ser Ser Val Phe Asp Met
            20                  25                  30

Tyr Trp Tyr Gln Gln Lys Pro Gly Gln Ser Pro Arg Pro Trp Ile Tyr
            35                  40                  45

Arg Thr Ser Asn Leu Ala Ser Gly Ile Pro Ala Arg Phe Ser Gly Ser
        50                  55                  60

Gly Ser Gly Thr Asp Phe Phe Leu Thr Ile Ser Ser Leu Glu Pro Glu
65                  70                  75                  80

Asp Ala Ala Val Tyr Tyr Cys Gln Gln Tyr Gln Ser Phe Pro Leu Thr
                85                  90                  95

Phe Gly Gln Gly Thr Lys Leu Glu Leu Lys
            100                 105

<210> SEQ ID NO 57
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 57

Glu Ile Val Leu Thr Gln Ser Pro Ala Thr Leu Ser Leu Ser Pro Gly
1               5                   10                  15

Glu Arg Val Thr Leu Ser Cys Ser Ala Ser Ser Ser Val Phe Asp Met
            20                  25                  30

Tyr Trp Tyr Gln Gln Lys Pro Gly Ser Ser Pro Arg Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Asp Phe Phe Leu Thr Ile Ser Ser Leu Glu Pro Glu
65                  70                  75                  80

Asp Ala Ala Val Tyr Tyr Cys Gln Gln Tyr Gln Ser Phe Pro Leu Thr
                85                  90                  95

Phe Gly Gln Gly Thr Lys Leu Glu Leu Lys
            100                 105

<210> SEQ ID NO 58
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 58

Glu Ile Val Leu Thr Gln Ser Pro Ala Thr Leu Ser Leu Ser Pro Gly
1               5                   10                  15

Glu Arg Val Thr Leu Ser Cys Ser Ala Ser Ser Ser Val Phe Asp Met
            20                  25                  30

Tyr Trp Tyr Gln Gln Lys Pro Gly Ser Ser Pro Arg Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Asp Tyr Phe Leu Thr Ile Ser Ser Met Glu Pro Glu
65                  70                  75                  80

Asp Ala Ala Thr Tyr Tyr Cys Gln Gln Tyr Gln Ser Phe Pro Leu Thr
                85                  90                  95

Phe Gly Gln Gly Thr Lys Leu Glu Leu Lys
            100                 105

```
<210> SEQ ID NO 59
<211> LENGTH: 107
<212> TYPE: PRT
<213> ORGANISM: Artificial Sequence
<220> FEATURE:
<223> OTHER INFORMATION: Humanized light chain variable domain

<400> SEQUENCE: 59

Asp Ile Gln Met Thr Gln Ser Pro Ser Ser Leu Ser Ala Ser Val Gly
 1               5                  10                  15

Asp Arg Val Thr Ile Ile Cys Arg Ala Ser Gln Glu Ile Ser Gly Tyr
            20                  25                  30

Leu Ser Trp Leu Gln Gln Lys Pro Asp Gly Thr Ile Lys Ser Leu Ile
        35                  40                  45

Tyr Ala Ala Ser Thr Leu Asp Pro Gly Val Pro Ser Arg Phe Ser Gly
    50                  55                  60

Ser Arg Ser Gly Ala Asp Phe Thr Leu Thr Ile Ser Ser Leu Gln Pro
65                  70                  75                  80

Glu Asp Phe Ala Thr Tyr Tyr Cys Leu Gln Tyr Ala Ile Tyr Pro Pro
                85                  90                  95

Thr Phe Gly Gln Gly Thr Lys Leu Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Humanized light chain variable domain

<400> SEQUENCE: 60

Asp Ile Gln Met Thr Gln Ser Pro Ser Ser Leu Ser Ala Ser Val Gly
 1               5                  10                  15

Asp Arg Val Thr Leu Ile Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Phe Ala Ala Ser Thr Leu Asp Pro Gly Val Pro Ser Arg Phe Ser Gly
    50                  55                  60

Ser Arg Ser Gly Ala Asp Phe Thr Leu Thr Ile Ser Ser Leu Gln Pro
65                  70                  75                  80

Glu Asp Phe Ala Asp Tyr Tyr Cys Leu Gln Tyr Ala Ile Tyr Pro Pro
                85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Humanized light chain variable domain

<400> SEQUENCE: 61

Asp Ile Gln Met Thr Gln Ser Pro Ser Ser Leu Ser Ala Ser Val Gly
 1               5                  10                  15

Asp Arg Val Thr Leu Ile Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45
```

```
Phe Ala Ala Ser Thr Leu Asp Pro Gly Val Pro Ser Arg Phe Ser Gly
        50                  55                  60

Ser Arg Ser Gly Ala Asp Tyr Thr Leu Thr Ile Ser Ser Leu Gln Pro
 65                  70                  75                  80

Glu Asp Phe Ala Asp Tyr Tyr Cys Leu Gln Tyr Ala Ile Tyr Pro Pro
                85                  90                  95

Thr Phe Gly Gln Gly Thr Lys Leu Glu Ile Lys
            100                 105
```

<210> SEQ ID NO 62
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 62

```
Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Phe Met
                20                  25                  30

His Trp Tyr Gln Gln Lys Pro Gly Leu Ala Pro Arg Lys Leu Ile Tyr
            35                  40                  45

Asp Thr Ser Lys Leu Ala Ser Gly Ile Pro Asp Arg Phe Ser Gly Ser
 50                  55                  60

Gly Ser Gly Thr Ser Tyr Thr Leu Thr Ile Ser Arg Leu Glu Pro Glu
 65                  70                  75                  80

Asp Phe Ala Val Tyr Tyr Cys Gln Gln Trp Thr Tyr Tyr Pro Pro Thr
                85                  90                  95

Phe Gly Gln Gly Thr Lys Val Glu Ile Lys
            100                 105
```

<210> SEQ ID NO 63
<211> LENGTH: 106
<212> TYPE: PRT
<213> ORGANISM: Artificial Sequence
<220> FEATURE:
<223> OTHER INFORMATION: Humanized light chain variable domain

<400> SEQUENCE: 63

```
Gln Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Phe Met
                20                  25                  30

His Trp Tyr Gln Gln Lys Pro Gly Leu Ala Pro Arg Lys Trp Ile Tyr
            35                  40                  45

Asp Thr Ser Lys Leu Ala Ser Gly Val Pro Asp Arg Phe Ser Gly Ser
 50                  55                  60

Gly Ser Gly Thr Ser Tyr Thr Leu Thr Ile Ser Arg Leu Glu Pro Glu
 65                  70                  75                  80

Asp Phe Ala Val Tyr Tyr Cys Gln Gln Trp Thr Tyr Tyr Pro Pro Thr
                85                  90                  95

Phe Gly Gln Gly Thr Lys Val Glu Ile Lys
            100                 105
```

<210> SEQ ID NO 64
<211> LENGTH: 107
<212> TYPE: PRT

<213> ORGANISM: Artificial Sequence
<220> FEATURE:
<223> OTHER INFORMATION: Humanized light chain variable domain

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Leu Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Val Gln Tyr Thr Ser His Pro Tyr
                85                  90                  95

Thr Phe Gly Gln Gly Thr Lys Val Glu Ile Lys
            100                 105

<210> SEQ ID NO 65
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 65

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Thr Ile Asn Tyr Asp Glu Lys Phe
50                  55                  60

Arg Ser Arg Val Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Thr Thr Gly Trp Asp Gly Glu His Trp Gly Gln Gly Thr Leu Thr
            100                 105                 110

Val Ser Ser
        115

<210> SEQ ID NO 66
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 66

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
        35                  40                  45

```
Gly Asn Ile Tyr Pro Gly Ser Gly Thr Ile Asn Tyr Asp Glu Lys Phe
        50                  55                  60

Arg Ser Arg Ala Thr Leu Thr Val Asp Thr Ser Ile Ser Thr Ala Tyr
 65                  70                  75                  80

Met Glu Val Ser Arg Leu Arg Ser Glu Asp Thr Ala Val Tyr Tyr Cys
                    85                  90                  95

Thr Thr Gly Trp Asp Gly Glu His Trp Gly Gln Gly Thr Thr Leu Thr
                100                 105                 110

Val Ser Ser
        115

<210> SEQ ID NO 67
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 67

Gln Val Gln Leu Val Gln Ser Gly Ala Glu Val Val Lys Pro Gly Ala
  1               5                  10                  15

Ser Val Lys Leu Ser Cys Lys Ala Ser Gly Tyr Thr Phe Thr Thr Phe
                20                  25                  30

Trp Met His Trp Val Lys Gln Ala Pro Gly Gln Gly Leu Glu Trp Ile
            35                  40                  45

Gly Asn Ile Tyr Pro Gly Ser Gly Thr Ile Asn Tyr Asp Glu Lys Phe
        50                  55                  60

Arg Ser Arg Ala Thr Leu Thr Val Asp Thr Ser Ile Ser Thr Ala Tyr
 65                  70                  75                  80

Met Glu Val Ser Arg Leu Arg Ser Glu Asp Thr Ala Val Tyr Tyr Cys
                    85                  90                  95

Thr Thr Gly Trp Asp Gly Glu His Trp Gly Gln Gly Thr Thr Leu Thr
                100                 105                 110

Val Ser Ser
        115

<210> SEQ ID NO 68
<211> LENGTH: 121
<212> TYPE: PRT
<213> ORGANISM: Artificial Sequence
<220> FEATURE:
<223> OTHER INFORMATION: Humanized heavy chain variable domain

<400> SEQUENCE: 68

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                20                  25                  30

Gly Met His Trp Ile Arg Gln Ala Pro Gly Lys Gly Leu Glu Trp Val
            35                  40                  45

Ser Tyr Ile Gly Thr Thr Ser Ser Ile Ile Tyr Tyr Ala Asp Thr Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg Arg Asp Tyr Gly Asn Tyr Tyr Trp Tyr Leu Asp Val Trp Gly
```

```
                    100                 105                 110
Gln Gly Thr Met Val Thr Val Ser Ser
            115                 120

<210> SEQ ID NO 69
<211> LENGTH: 121
<212> TYPE: PRT
<213> ORGANISM: Artificial Sequence
<220> FEATURE:
<223> OTHER INFORMATION: Humanized heavy chain variable domain

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Ile Arg Gln Ala Pro Gly Lys Gly Leu Glu Trp Ile
        35                  40                  45

Ala Tyr Ile Gly Thr Thr Ser Ser Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Asp Tyr Gly Asn Tyr Tyr Trp Tyr Leu Asp Val Trp Gly
            100                 105                 110

Thr Gly Thr Met Val Thr Val Ser Ser
            115                 120

<210> SEQ ID NO 70
<211> LENGTH: 121
<212> TYPE: PRT
<213> ORGANISM: Artificial Sequence
<220> FEATURE:
<223> OTHER INFORMATION: Humanized heavy chain variable domain

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Ile Arg Gln Ala Pro Gly Lys Gly Leu Glu Trp Ile
        35                  40                  45

Ala Tyr Ile Gly Thr Thr Ser Ser Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Arg Asp Tyr Gly Asn Tyr Tyr Trp Tyr Leu Asp Val Trp Gly
            100                 105                 110

Thr Gly Thr Met Val Thr Val Ser Ser
            115                 120

<210> SEQ ID NO 71
<211> LENGTH: 115
<212> TYPE: PRT
<213> ORGANISM: Artificial Sequence
<220> FEATURE:
```

<223> OTHER INFORMATION: Humanized heavy chain variable domain

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met His Trp Val Gln Gln Ala Pro Gly Gln Arg Leu Glu Trp Met
        35                  40                  45

Gly Arg Ile Asp Pro Met Asn Gly Asn Ser Lys Tyr Asp Pro Lys Phe
    50                  55                  60

Gln Asp Arg Val Thr Ile Thr Ala Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser
        115

<210> SEQ ID NO 72
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met His Trp Val Gln Gln Ala Pro Gly Gln Arg Leu Glu Trp Met
        35                  40                  45

Gly Arg Ile Asp Pro Met Asn Ala Asn Ser Lys Tyr Asp Pro Lys Phe
    50                  55                  60

Gln Asp Arg Val Thr Ile Thr Ala Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser
        115

<210> SEQ ID NO 73
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 73

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asn Ile Lys Asp Thr
            20                  25                  30

Tyr Met His Trp Val Gln Gln Ala Pro Glu Gln Arg Leu Glu Trp Met

```
                35                  40                  45
Gly Arg Ile Asp Pro Met Asn Ala Asn Ser Lys Tyr Asp Pro Lys Phe
 50                  55                  60

Gln Asp Arg Val Thr Ile Thr Ala Asp Thr Ser Ala Ser Thr Ala Tyr
 65                  70                  75                  80

Leu Glu Leu Ser Ser Leu Arg Ser Glu Asp Thr Ala Val Tyr Tyr Cys
                 85                  90                  95

Thr Ser Ser Lys Trp Gly Asp Tyr Trp Gly Gln Gly Thr Leu Leu Thr
                100                 105                 110

Val Ser Ser
        115

<210> SEQ ID NO 74
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 74

Gln Val Gln Leu Val Gln Ser Gly Ala Glu Val Lys Lys Pro Gly Ala
 1               5                  10                  15

Ser Val Lys Leu Ser Cys Lys Ala Ser Gly Phe Asn Ile Lys Asp Thr
                 20                  25                  30

Tyr Met His Trp Val Gln Gln Ala Pro Glu Gln Arg Leu Glu Trp Ile
                 35                  40                  45

Gly Arg Ile Asp Pro Met Asn Ala Asn Ser Lys Tyr Asp Pro Lys Phe
 50                  55                  60

Gln Asp Arg Ala Thr Ile Thr Ala Asp Thr Ser Ala Asn Thr Ala Tyr
 65                  70                  75                  80

Leu Glu Leu Ser Ser Leu Arg Ser Glu Asp Thr Ala Val Tyr Tyr Cys
                 85                  90                  95

Thr Ser Ser Lys Trp Gly Asp Tyr Trp Gly Gln Gly Thr Leu Leu Thr
                100                 105                 110

Val Ser Ser
        115

<210> SEQ ID NO 75
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 75

Gln Val Gln Leu Gln Gln Ser Gly Ala Glu Val Lys Lys Pro Gly Ala
 1               5                  10                  15

Ser Val Lys Leu Ser Cys Thr Ala Ser Gly Phe Asn Ile Lys Asp Thr
                 20                  25                  30

Tyr Met His Trp Val Gln Gln Ala Pro Glu Gln Arg Leu Glu Trp Ile
                 35                  40                  45

Gly Arg Ile Asp Pro Met Asn Gly Asn Ser Lys Tyr Asp Pro Lys Phe
 50                  55                  60

Gln Asp Arg Ala Thr Ile Thr Ala Asp Thr Ser Ala Asn Thr Ala Tyr
 65                  70                  75                  80

Leu Glu Leu Ser Ser Leu Arg Ser Glu Asp Thr Ala Val Tyr Tyr Cys
                 85                  90                  95
```

Thr Ser Ser Lys Trp Gly Asp Tyr Trp Gly Gln Gly Thr Leu Leu Thr
            100                 105                 110

Val Ser Ser
        115

<210> SEQ ID NO 76
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 76

Gln Val Gln Leu Gln Gln Ser Gly Ala Glu Val Lys Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Gln Gln Ala Pro Glu Gln Arg Leu Glu Trp Ile
            35                  40                  45

Gly Arg Ile Asp Pro Met Asn Ala Asn Ser Lys Tyr Asp Pro Lys Phe
        50                  55                  60

Gln Asp Arg Ala Thr Ile Thr Ala Asp Thr Ser Ala Asn Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser
        115

<210> SEQ ID NO 77
<211> LENGTH: 121
<212> TYPE: PRT
<213> ORGANISM: Artificial Sequence
<220> FEATURE:
<223> OTHER INFORMATION: Humanized heavy chain variable domain

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ile Lys Asp Tyr
            20                  25                  30

Tyr Ile His Trp Val Arg Gln Ala Pro Gly Gln Gly Leu Glu Trp Ile
            35                  40                  45

Gly Trp Ile Asp Pro Asp Asn Gly Asn Thr Lys Tyr Asp Pro Asn Phe
        50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Gly Tyr Gly Gly Phe Tyr Thr Met Asp Tyr Trp Gly
            100                 105                 110

Gln Gly Thr Leu Val Thr Val Ser Ser
        115                 120

<210> SEQ ID NO 78
<211> LENGTH: 121
<212> TYPE: PRT
<213> ORGANISM: Artificial Sequence
<220> FEATURE:
<223> OTHER INFORMATION: Humanized light chain variable domain

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Asp Asn Gly Asn Thr Lys Tyr Asp Pro Asn Phe
    50                  55                  60

Gln Gly Arg Ala Thr Met Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Gly Tyr Gly Gly Phe Tyr Thr Met Asp Tyr Trp Gly
            100                 105                 110

Gln Gly Thr Leu Val Thr Val Ser Ser
        115                 120

<210> SEQ ID NO 79
<211> LENGTH: 119
<212> TYPE: PRT
<213> ORGANISM: Artificial Sequence
<220> FEATURE:
<223> OTHER INFORMATION: Humanized heavy chain variable domain

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Asp Thr Lys Tyr Thr Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Asn Trp Asp Gly Phe Ala Tyr Trp Gly Gln Gly
            100                 105                 110

Thr Leu Val Thr Val Ser Ser
        115

<210> SEQ ID NO 80
<211> LENGTH: 119
<212> TYPE: PRT
<213> ORGANISM: Artificial Sequence
<220> FEATURE:
<223> OTHER INFORMATION: Humanized heavy chain variable domain

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Met His Trp Val Lys Gln Arg Pro Gly Gln Gly Leu Glu Trp Ile
            35                  40                  45

Gly Arg Ile Asp Pro Asn Ser Gly Asp Thr Lys Tyr Thr Glu Lys Phe
 50                  55                  60

Lys Asn Arg Ala Thr Leu Thr Val Asp Lys Ser Thr Ser Thr Ala Tyr
65                   70                  75                  80

Met Glu Phe Ser Ser Leu Arg Ser Glu Asp Thr Ala Val Tyr Tyr Cys
                 85                  90                  95

Ala Arg Gly Gly Pro Asn Trp Asp Gly Phe Ala Tyr Trp Gly Gln Gly
            100                 105                 110

Thr Leu Val Thr Val Ser Ser
        115

<210> SEQ ID NO 81
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 81

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
            35                  40                  45

Gly Asn Ile Tyr Pro Gly Ser Gly Ile Ser Asn Tyr Asp Glu Lys Phe
 50                  55                  60

Lys Asn Arg Val Thr Leu Thr Val Asp Thr Ser Ile Ser Thr Ala Tyr
65                   70                  75                  80

Met Glu Leu Ser Arg Leu Arg Ser Glu Asp Thr Ala Val Tyr Tyr Cys
                 85                  90                  95

Thr Thr Gly Trp Asp Gly Glu His Trp Gly Gln Gly Thr Thr Leu Thr
            100                 105                 110

Val Ser Ser
        115

<210> SEQ ID NO 82
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 82

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
            35                  40                  45

Gly Asn Ile Tyr Pro Gly Ser Gly Ile Ser Asn Tyr Asp Glu Lys Phe
 50                  55                  60

Lys Asn Arg Ala Thr Leu Thr Val Asp Thr Ser Ile Ser Thr Ala Tyr
65                   70                  75                  80

Met Glu Val Ser Arg Leu Arg Ser Glu Asp Thr Ala Val Tyr Tyr Cys
                 85                  90                  95

```
Thr Thr Gly Trp Asp Gly Glu His Trp Gly Gln Gly Thr Thr Leu Thr
            100                 105                 110

Val Ser Ser
        115

<210> SEQ ID NO 83
<211> LENGTH: 115
<212> TYPE: PRT
<213> ORGANISM: Artificial Sequence
<220> FEATURE:
<223> OTHER INFORMATION: Humanized heavy chain variable domain

<400> SEQUENCE: 83

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Lys Gln Ala Pro Gly Gln Gly Leu Glu Trp Ile
        35                  40                  45

Gly Asn Ile Tyr Pro Gly Ser Gly Ile Ser Asn Tyr Asp Glu Lys Phe
    50                  55                  60

Lys Asn Arg Ala Thr Leu Thr Val Asp Thr Ser Ile Ser Thr Ala Tyr
65                  70                  75                  80

Met Glu Val Ser Arg Leu Arg Ser Glu Asp Thr Ala Val Tyr Tyr Cys
                85                  90                  95

Thr Thr Gly Trp Asp Gly Glu His Trp Gly Gln Gly Thr Thr Leu Thr
            100                 105                 110

Val Ser Ser
        115

<210> SEQ ID NO 84
<211> LENGTH: 215
<212> TYPE: PRT
<213> ORGANISM: Artificial Sequence
<220> FEATURE:
<223> OTHER INFORMATION: Humanized light chains

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
```

```
                145                 150                 155                 160
        Gln Glu Ser Val Thr Glu Gln Asp Ser Lys Asp Ser Thr Tyr Ser Leu
                        165                 170                 175

Ser Ser Thr Leu Thr Leu Ser Lys Ala Asp Tyr Glu Lys His Lys Val
                        180                 185                 190

Tyr Ala Cys Glu Val Thr His Gln Gly Leu Ser Ser Pro Val Thr Lys
                        195                 200                 205

Ser Phe Asn Arg Gly Glu Cys
                        210                 215

<210> SEQ ID NO 85
<211> LENGTH: 215
<212> TYPE: PRT
<213> ORGANISM: Artificial Sequence
<220> FEATURE:
<223> OTHER INFORMATION: Humanized light chains

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
                20                  25                  30

Leu Ala Trp Tyr Gln Gln Lys Pro Gly Lys Ala Pro Gln Leu Leu Val
            35                  40                  45

Tyr Gly Ala Thr Asn Leu Ala Asp Gly Val Pro Ser Arg Phe Ser Gly
        50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 86
<211> LENGTH: 215
<212> TYPE: PRT
<213> ORGANISM: Artificial Sequence
<220> FEATURE:
<223> OTHER INFORMATION: Humanized light chains

<400> SEQUENCE: 86

Asp Ile Gln Met Thr Gln Ser Pro Ser Ser Leu Ser Val Ser Val Gly
1               5                   10                  15
```

-continued

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Ala Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 87
<211> LENGTH: 215
<212> TYPE: PRT
<213> ORGANISM: Artificial Sequence
<220> FEATURE:
<223> OTHER INFORMATION: Humanized light chains

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Lys Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Val Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 88
<211> LENGTH: 215
<212> TYPE: PRT
<213> ORGANISM: Artificial Sequence
<220> FEATURE:
<223> OTHER INFORMATION: Humanized light chains

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile His Ser Asn
            20                  25                  30

Leu Ala Trp Tyr Gln Gln Lys Pro Gly Lys Ala Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Ala Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Tyr Val Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 89
<211> LENGTH: 215
<212> TYPE: PRT
<213> ORGANISM: Artificial Sequence
<220> FEATURE:
<223> OTHER INFORMATION: Humanized light chains

<400> SEQUENCE: 89

Asp Ile Gln Met Thr Gln Ser Pro Ser Ser Leu Ser Val Ser Val Gly
1               5                   10                  15

Asp Arg Val Thr Ile Thr Cys Arg Ala Ser Glu Asn Ile His Ser Asn
            20                  25                  30

```
Leu Ala Trp Tyr Gln Gln Lys Pro Gly Lys Ala Pro Gln Leu Leu Val
            35                  40                  45

Tyr Gly Ala Thr Asn Leu Ala Asp Gly Val Pro Ser Arg Phe Ser Gly
     50                  55                  60

Ser Gly Ser Gly Ala Gln Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Pro
                 85                  90                  95

Tyr Val Phe Gly Gly Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 90
<211> LENGTH: 213
<212> TYPE: PRT
<213> ORGANISM: Artificial Sequence
<220> FEATURE:
<223> OTHER INFORMATION: Humanized light chains

<400> SEQUENCE: 90

Glu Ile Val Leu Thr Gln Ser Pro Ala Thr Leu Ser Leu Ser Pro Gly
1                5                  10                  15

Glu Arg Ala Thr Leu Ser Cys Ser Ala Ser Ser Ser Val Phe Asp Met
            20                  25                  30

Tyr Trp Tyr Gln Gln Lys Pro Gly Gln Ser Pro Arg Pro Trp Ile Tyr
            35                  40                  45

Arg Thr Ser Asn Leu Ala Ser Gly Ile Pro Ala Arg Phe Ser Gly Ser
     50                  55                  60

Gly Ser Gly Thr Asp Phe Phe Leu Thr Ile Ser Ser Leu Glu Pro Glu
 65                  70                  75                  80

Asp Phe Ala Val Tyr Tyr Cys Gln Gln Tyr Gln Ser Pro Leu Thr
                 85                  90                  95

Phe Gly Gln Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 91
<211> LENGTH: 213
<212> TYPE: PRT
<213> ORGANISM: Artificial Sequence
<220> FEATURE:
<223> OTHER INFORMATION: Humanized light chains

<400> SEQUENCE: 91

```
Glu Ile Val Leu Thr Gln Ser Pro Ala Thr Leu Ser Leu Ser Pro Gly
1               5                   10                  15

Glu Arg Val Thr Leu Ser Cys Ser Ala Ser Ser Ser Val Phe Asp Met
            20                  25                  30

Tyr Trp Tyr Gln Gln Lys Pro Gly Gln Ser Pro Arg Pro Trp Ile Tyr
        35                  40                  45

Arg Thr Ser Asn Leu Ala Ser Gly Ile Pro Ala Arg Phe Ser Gly Ser
    50                  55                  60

Gly Ser Gly Thr Asp Phe Phe Leu Thr Ile Ser Ser Leu Glu Pro Glu
65                  70                  75                  80

Asp Ala Ala Val Tyr Tyr Cys Gln Gln Tyr Gln Ser Phe Pro Leu Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 92
<211> LENGTH: 213
<212> TYPE: PRT
<213> ORGANISM: Artificial Sequence
<220> FEATURE:
<223> OTHER INFORMATION: Humanized light chains

<400> SEQUENCE: 92

```
Glu Ile Val Leu Thr Gln Ser Pro Ala Thr Leu Ser Leu Ser Pro Gly
1               5                   10                  15

Glu Arg Val Thr Leu Ser Cys Ser Ala Ser Ser Ser Val Phe Asp Met
            20                  25                  30

Tyr Trp Tyr Gln Gln Lys Pro Gly Ser Ser Pro Arg Pro Trp Ile Tyr
```

```
            35                  40                  45
Arg Thr Ser Asn Leu Ala Ser Gly Val Pro Ala Arg Phe Ser Gly Ser
 50                  55                  60

Gly Ser Gly Thr Asp Phe Phe Leu Thr Ile Ser Ser Leu Glu Pro Glu
 65                  70                  75                  80

Asp Ala Ala Val Tyr Tyr Cys Gln Gln Tyr Gln Ser Phe Pro Leu Thr
                 85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 93
<211> LENGTH: 213
<212> TYPE: PRT
<213> ORGANISM: Artificial Sequence
<220> FEATURE:
<223> OTHER INFORMATION: Humanized light chains

<400> SEQUENCE: 93

Glu Ile Val Leu Thr Gln Ser Pro Ala Thr Leu Ser Leu Ser Pro Gly
 1               5                  10                  15

Glu Arg Val Thr Leu Ser Cys Ser Ala Ser Ser Ser Val Phe Asp Met
            20                  25                  30

Tyr Trp Tyr Gln Gln Lys Pro Gly Ser Ser Pro Arg Pro Trp Ile Tyr
        35                  40                  45

Arg Thr Ser Asn Leu Ala Ser Gly Val Pro Ala Arg Phe Ser Gly Ser
 50                  55                  60

Gly Ser Gly Thr Asp Tyr Phe Leu Thr Ile Ser Ser Met Glu Pro Glu
 65                  70                  75                  80

Asp Ala Ala Thr Tyr Tyr Cys Gln Gln Tyr Gln Ser Phe Pro Leu Thr
                 85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
```

```
                180               185               190
Cys Glu Val Thr His Gln Gly Leu Ser Ser Pro Val Thr Lys Ser Phe
                195               200               205

Asn Arg Gly Glu Cys
        210

<210> SEQ ID NO 94
<211> LENGTH: 214
<212> TYPE: PRT
<213> ORGANISM: Artificial Sequence
<220> FEATURE:
<223> OTHER INFORMATION: Humanized light chains

<400> SEQUENCE: 94

Asp Ile Gln Met Thr Gln Ser Pro Ser Ser Leu Ser Ala Ser Val Gly
1               5                   10                  15

Asp Arg Val Thr Ile Ile Cys Arg Ala Ser Gln Glu Ile Ser Gly Tyr
            20                  25                  30

Leu Ser Trp Leu Gln Gln Lys Pro Asp Gly Thr Ile Lys Ser Leu Ile
        35                  40                  45

Tyr Ala Ala Ser Thr Leu Asp Pro Gly Val Pro Ser Arg Phe Ser Gly
50                  55                  60

Ser Arg Ser Gly Ala Asp Phe Thr Leu Thr Ile Ser Ser Leu Gln Pro
65                  70                  75                  80

Glu Asp Phe Ala Thr Tyr Tyr Cys Leu Gln Tyr Ala Ile Tyr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 95
<211> LENGTH: 214
<212> TYPE: PRT
<213> ORGANISM: Artificial Sequence
<220> FEATURE:
<223> OTHER INFORMATION: Humanized light chains

<400> SEQUENCE: 95

Asp Ile Gln Met Thr Gln Ser Pro Ser Ser Leu Ser Ala Ser Val Gly
1               5                   10                  15

Asp Arg Val Thr Leu Ile Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45
```

```
Phe Ala Ala Ser Thr Leu Asp Pro Gly Val Pro Ser Arg Phe Ser Gly
 50                  55                  60

Ser Arg Ser Gly Ala Asp Phe Thr Leu Thr Ile Ser Ser Leu Gln Pro
 65                  70                  75                  80

Glu Asp Phe Ala Asp Tyr Tyr Cys Leu Gln Tyr Ala Ile Tyr Pro Pro
                 85                  90                  95

Thr Phe Gly Gln Gly Thr Lys Leu Glu Ile Lys Arg Thr Val Ala Ala
                 100                 105                 110

Pro Ser Val Phe Ile Phe Pro Pro Ser Asp Glu Gln Leu Lys Ser Gly
                 115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
 145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
                 180                 185                 190

Ala Cys Glu Val Thr His Gln Gly Leu Ser Ser Pro Val Thr Lys Ser
                 195                 200                 205

Phe Asn Arg Gly Glu Cys
 210

<210> SEQ ID NO 96
<211> LENGTH: 214
<212> TYPE: PRT
<213> ORGANISM: Artificial Sequence
<220> FEATURE:
<223> OTHER INFORMATION: Humanized light chains

<400> SEQUENCE: 96

Asp Ile Gln Met Thr Gln Ser Pro Ser Ser Leu Ser Ala Ser Val Gly
 1                5                  10                  15

Asp Arg Val Thr Leu Ile Cys Arg Ala Ser Gln Glu Ile Ser Gly Tyr
                 20                  25                  30

Leu Ser Trp Leu Gln Gln Lys Pro Asp Gly Thr Ile Lys Arg Leu Ile
                 35                  40                  45

Phe Ala Ala Ser Thr Leu Asp Pro Gly Val Pro Ser Arg Phe Ser Gly
 50                  55                  60

Ser Arg Ser Gly Ala Asp Tyr Thr Leu Thr Ile Ser Ser Leu Gln Pro
 65                  70                  75                  80

Glu Asp Phe Ala Asp Tyr Tyr Cys Leu Gln Tyr Ala Ile Tyr Pro Pro
                 85                  90                  95

Thr Phe Gly Gln Gly Thr Lys Leu Glu Ile Lys Arg Thr Val Ala Ala
                 100                 105                 110

Pro Ser Val Phe Ile Phe Pro Pro Ser Asp Glu Gln Leu Lys Ser Gly
                 115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
 145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
                 180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 97
<211> LENGTH: 213
<212> TYPE: PRT
<213> ORGANISM: Artificial Sequence
<220> FEATURE:
<223> OTHER INFORMATION: Humanized light chains

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Phe Met
            20                  25                  30

His Trp Tyr Gln Gln Lys Pro Gly Leu Ala Pro Arg Lys Leu Ile Tyr
        35                  40                  45

Asp Thr Ser Lys Leu Ala Ser Gly Ile Pro Asp Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Phe Ala Val Tyr Tyr Cys Gln Gln Trp Thr Tyr Tyr Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 98
<211> LENGTH: 213
<212> TYPE: PRT
<213> ORGANISM: Artificial Sequence
<220> FEATURE:
<223> OTHER INFORMATION: Humanized light chains

<400> SEQUENCE: 98

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Phe Met
            20                  25                  30

His Trp Tyr Gln Gln Lys Pro Gly Leu Ala Pro Arg Lys Trp Ile Tyr
        35                  40                  45

Asp Thr Ser Lys Leu Ala Ser Gly Val Pro Asp Arg Phe Ser Gly Ser
    50                  55                  60

```
Gly Ser Gly Thr Ser Tyr Thr Leu Thr Ile Ser Arg Leu Glu Pro Glu
 65                  70                  75                  80

Asp Phe Ala Val Tyr Tyr Cys Gln Gln Trp Thr Tyr Pro Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 99
<211> LENGTH: 214
<212> TYPE: PRT
<213> ORGANISM: Artificial Sequence
<220> FEATURE:
<223> OTHER INFORMATION: Humanized light chains

<400> SEQUENCE: 99

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Ser Val Tyr
             20                  25                  30

Leu Ser Trp Leu Gln Gln Lys Pro Gly Lys Ala Pro Lys Arg Leu Ile
         35                  40                  45

Tyr Ala Ala Ser Thr Leu Asp Ser Gly Val Pro Ser Arg Phe Ser Gly
     50                  55                  60

Ser Gly Ser Gly Ser Asp Tyr Thr Leu Thr Ile Ser Ser Leu Gln Pro
 65                  70                  75                  80

Glu Asp Phe Ala Thr Tyr Tyr Cys Val Gln Tyr Thr Ser His Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 100
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 100

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Thr Ile Asn Tyr Asp Glu Lys Phe
    50                  55                  60

Arg Ser Arg Val Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Thr Thr Gly Trp Asp Gly Glu His Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

-continued

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 101
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 101

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Thr Ile Asn Tyr Asp Glu Lys Phe
50                  55                  60

Arg Ser Arg Ala Thr Leu Thr Val Asp Thr Ser Ile Ser Thr Ala Tyr
65                  70                  75                  80

Met Glu Val Ser Arg Leu Arg Ser Glu Asp Thr Ala Val Tyr Tyr Cys
                85                  90                  95

Thr Thr Gly Trp Asp Gly Glu His Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

```
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 102
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 102

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Lys Gln Ala Pro Gly Gln Gly Leu Glu Trp Ile
        35                  40                  45

Gly Asn Ile Tyr Pro Gly Ser Gly Thr Ile Asn Tyr Asp Glu Lys Phe
    50                  55                  60

Arg Ser Arg Ala Thr Leu Thr Val Asp Thr Ser Ile Ser Thr Ala Tyr
65                  70                  75                  80

Met Glu Val Ser Arg Leu Arg Ser Glu Asp Thr Ala Val Tyr Tyr Cys
                85                  90                  95

Thr Thr Gly Trp Asp Gly Glu His Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 103
<211> LENGTH: 451
<212> TYPE: PRT
<213> ORGANISM: Artificial Sequence
<220> FEATURE:
<223> OTHER INFORMATION: Humanized heavy chains

<400> SEQUENCE: 103

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Gly Met His Trp Ile Arg Gln Ala Pro Gly Lys Gly Leu Glu Trp Val
        35                  40                  45
Ser Tyr Ile Gly Thr Thr Ser Ser Ile Ile Tyr Tyr Ala Asp Thr Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Asp Tyr Gly Asn Tyr Tyr Trp Tyr Leu Asp Val Trp Gly
            100                 105                 110
```

```
Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 104
<211> LENGTH: 451
<212> TYPE: PRT
<213> ORGANISM: Artificial Sequence
<220> FEATURE:
<223> OTHER INFORMATION: Humanized heavy chains

<400> SEQUENCE: 104

Glu Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Asp Tyr
            20                  25                  30

Gly Met His Trp Ile Arg Gln Ala Pro Gly Lys Gly Leu Glu Trp Ile
            35                  40                  45

Ala Tyr Ile Gly Thr Thr Ser Ser Ile Ile Tyr Tyr Ala Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Arg Asp Tyr Gly Asn Tyr Tyr Trp Tyr Leu Asp Val Trp Gly
            100                 105                 110

Thr Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
              435                 440                 445

Pro Gly Lys
       450

<210> SEQ ID NO 105
<211> LENGTH: 451
<212> TYPE: PRT
<213> ORGANISM: Artificial Sequence
<220> FEATURE:
<223> OTHER INFORMATION: Humanized heavy chains

<400> SEQUENCE: 105

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met His Trp Ile Arg Gln Ala Pro Gly Lys Gly Leu Glu Trp Ile
        35                  40                  45

Ala Tyr Ile Gly Thr Thr Ser Ser Ile Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Arg Asp Tyr Gly Asn Tyr Tyr Trp Tyr Leu Asp Val Trp Gly
            100                 105                 110

Thr Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 106
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Met His Trp Val Gln Gln Ala Pro Gly Gln Arg Leu Glu Trp Met
            35                  40                  45

Gly Arg Ile Asp Pro Met Asn Gly Asn Ser Lys Tyr Asp Pro Lys Phe
        50                  55                  60

Gln Asp Arg Val Thr Ile Thr Ala Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 107
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met His Trp Val Gln Gln Ala Pro Gly Gln Arg Leu Glu Trp Met
        35                  40                  45

Gly Arg Ile Asp Pro Met Asn Ala Asn Ser Lys Tyr Asp Pro Lys Phe
    50                  55                  60

Gln Asp Arg Val Thr Ile Thr Ala Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 108
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 108

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asn Ile Lys Asp Thr
            20                  25                  30

Tyr Met His Trp Val Gln Gln Ala Pro Glu Gln Arg Leu Glu Trp Met
            35                  40                  45

Gly Arg Ile Asp Pro Met Asn Ala Asn Ser Lys Tyr Asp Pro Lys Phe
        50                  55                  60

Gln Asp Arg Val Thr Ile Thr Ala Asp Thr Ser Ala Ser Thr Ala Tyr
65                  70                  75                  80
```

```
Leu Glu Leu Ser Ser Leu Arg Ser Glu Asp Thr Ala Val Tyr Tyr Cys
                 85                  90                  95

Thr Ser Ser Lys Trp Gly Asp Tyr Trp Gly Gln Gly Thr Leu Leu Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130             135                 140

Lys Asp Tyr Phe Pro Glu Pro Val Thr Val Ser Trp Asn Ser Gly Ala
145             150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210             215                 220

Pro Pro Cys Pro Ala Pro Glu Leu Leu Gly Gly Pro Ser Val Phe Leu
225             230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290             295                 300

Thr Val Leu His Gln Asp Trp Leu Asn Gly Lys Glu Tyr Lys Cys Lys
305             310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385             390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 109
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 109
```

-continued

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asn Ile Lys Asp Thr
            20                  25                  30

Tyr Met His Trp Val Gln Gln Ala Pro Glu Gln Arg Leu Glu Trp Ile
        35                  40                  45

Gly Arg Ile Asp Pro Met Asn Ala Asn Ser Lys Tyr Asp Pro Lys Phe
    50                  55                  60

Gln Asp Arg Ala Thr Ile Thr Ala Asp Thr Ser Ala Asn Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn

```
                    420             425             430
His Tyr Thr Gln Lys Ser Leu Ser Leu Ser Pro Gly Lys
        435             440             445

<210> SEQ ID NO 110
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 110

Gln Val Gln Leu Gln Gln Ser Gly Ala Glu Val Lys Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Gln Gln Ala Pro Glu Gln Arg Leu Glu Trp Ile
        35                  40                  45

Gly Arg Ile Asp Pro Met Asn Gly Asn Ser Lys Tyr Asp Pro Lys Phe
    50                  55                  60

Gln Asp Arg Ala Thr Ile Thr Ala Asp Thr Ser Ala Asn Thr Ala Tyr
65                  70                  75                  80

Leu Glu Leu Ser Ser Leu Arg Ser Glu Asp Thr Ala Val Tyr Tyr Cys
                85                  90                  95

Thr Ser Ser Lys Trp Gly Asp Tyr Trp Gly Gln Gly Thr Leu Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

```
                   340                 345                 350
Arg Asp Glu Leu Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
                435                 440                 445

<210> SEQ ID NO 111
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 111

Gln Val Gln Leu Gln Gln Ser Gly Ala Glu Val Lys Lys Pro Gly Ala
1               5                   10                  15
Ser Val Lys Leu Ser Cys Thr Ala Ser Gly Phe Asn Ile Lys Asp Thr
                20                  25                  30
Tyr Met His Trp Val Gln Gln Ala Pro Glu Gln Arg Leu Glu Trp Ile
            35                  40                  45
Gly Arg Ile Asp Pro Met Asn Ala Asn Ser Lys Tyr Asp Pro Lys Phe
        50                  55                  60
Gln Asp Arg Ala Thr Ile Thr Ala Asp Thr Ser Ala Asn Thr Ala Tyr
65                  70                  75                  80
Leu Glu Leu Ser Ser Leu Arg Ser Glu Asp Thr Ala Val Tyr Tyr Cys
                85                  90                  95
Thr Ser Ser Lys Trp Gly Asp Tyr Trp Gly Gln Gly Thr Leu Leu Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
```

```
                   260                 265                 270
Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 112
<211> LENGTH: 451
<212> TYPE: PRT
<213> ORGANISM: Artificial Sequence
<220> FEATURE:
<223> OTHER INFORMATION: Humanized heavy chains

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Asp Asn Gly Asn Thr Lys Tyr Asp Pro Asn Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Gly Tyr Gly Phe Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                180             185             190
Pro Ser Ser Ser Leu Gly Thr Gln Thr Tyr Ile Cys Asn Val Asn His
            195             200             205

Lys Pro Ser Asn Thr Lys Val Asp Lys Val Glu Pro Lys Ser Cys
210             215             220

Asp Lys Thr His Thr Cys Pro Pro Cys Pro Ala Pro Glu Leu Leu Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
            290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Pro Ala Pro Ile
            325             330             335

Glu Lys Thr Ile Ser Lys Ala Lys Gly Gln Pro Arg Glu Pro Gln Val
            340             345             350

Tyr Thr Leu Pro Pro Ser Arg Asp Glu Leu Thr Lys Asn Gln Val Ser
            355             360             365

Leu Thr Cys Leu Val Lys Gly Phe Tyr Pro Ser Asp Ile Ala Val Glu
370             375             380

Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Lys
    450

<210> SEQ ID NO 113
<211> LENGTH: 451
<212> TYPE: PRT
<213> ORGANISM: Artificial Sequence
<220> FEATURE:
<223> OTHER INFORMATION: Humanized heavy chains

<400> SEQUENCE: 113

Gln Val Gln Leu Val Gln Ser Gly Ala Glu Val Lys Lys Pro Gly Ala
1               5               10              15

Ser Val Lys Val Ser Cys Lys Ala Ser Gly Phe Asn Ile Lys Asp Tyr
            20              25              30

Tyr Ile His Trp Val Arg Gln Ala Pro Gly Gln Gly Leu Glu Trp Ile
        35              40              45

Gly Trp Ile Asp Pro Asp Asn Gly Asn Thr Lys Tyr Asp Pro Asn Phe
    50              55              60

Gln Gly Arg Ala Thr Met Thr Ala Asp Thr Ser Thr Ser Thr Val Tyr
65              70              75              80

Met Glu Leu Ser Ser Leu Arg Ser Glu Asp Thr Ala Val Tyr Tyr Cys
```

```
                     85                  90                  95
Ala Arg Tyr Gly Gly Tyr Gly Gly Phe Tyr Thr Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 114
<211> LENGTH: 449
<212> TYPE: PRT
<213> ORGANISM: Artificial Sequence
<220> FEATURE:
<223> OTHER INFORMATION: Humanized heavy chains
```

<400> SEQUENCE: 114

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Asp Thr Lys Tyr Thr Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Asn Trp Asp Gly Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 115
<211> LENGTH: 449
<212> TYPE: PRT
<213> ORGANISM: Artificial Sequence
<220> FEATURE:
<223> OTHER INFORMATION: Humanized heavy chains

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Met His Trp Val Lys Gln Arg Pro Gly Gln Gly Leu Glu Trp Ile
        35                  40                  45

Gly Arg Ile Asp Pro Asn Ser Gly Asp Thr Lys Tyr Thr Glu Lys Phe
    50                  55                  60

Lys Asn Arg Ala Thr Leu Thr Val Asp Lys Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Ala Arg Gly Gly Pro Asn Trp Asp Gly Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 116
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 116

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Thr Phe
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Ile Ser Asn Tyr Asp Glu Lys Phe
    50                  55                  60

Lys Asn Arg Val Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Thr Thr Gly Trp Asp Gly Glu His Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu

```
                    225                 230                 235                 240

Phe Pro Pro Lys Pro Lys Asp Thr Leu Met Ile Ser Arg Thr Pro Glu
                            245                 250                 255

Val Thr Cys Val Val Val Asp Val Ser His Glu Asp Pro Glu Val Lys
                            260                 265                 270

Phe Asn Trp Tyr Val Asp Gly Val Glu Val His Asn Ala Lys Thr Lys
                            275                 280                 285

Pro Arg Glu Glu Gln Tyr Asn Ser Thr Tyr Arg Val Val Ser Val Leu
                            290                 295                 300

Thr Val Leu His Gln Asp Trp Leu Asn Gly Lys Glu Tyr Lys Cys Lys
            305                 310                 315                 320

Val Ser Asn Lys Ala Leu Pro Ala Pro Ile Glu Lys Thr Ile Ser Lys
                            325                 330                 335

Ala Lys Gly Gln Pro Arg Glu Pro Gln Val Tyr Thr Leu Pro Pro Ser
                            340                 345                 350

Arg Asp Glu Leu Thr Lys Asn Gln Val Ser Leu Thr Cys Leu Val Lys
                            355                 360                 365

Gly Phe Tyr Pro Ser Asp Ile Ala Val Glu Trp Glu Ser Asn Gly Gln
                            370                 375                 380

Pro Glu Asn Asn Tyr Lys Thr Thr Pro Pro Val Leu Asp Ser Asp Gly
            385                 390                 395                 400

Ser Phe Phe Leu Tyr Ser Lys Leu Thr Val Asp Lys Ser Arg Trp Gln
                            405                 410                 415

Gln Gly Asn Val Phe Ser Cys Ser Val Met His Glu Ala Leu His Asn
                            420                 425                 430

His Tyr Thr Gln Lys Ser Leu Ser Leu Ser Pro Gly Lys
                            435                 440                 445

<210> SEQ ID NO 117
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 117

Gln Val Gln Leu Val Gln Ser Gly Ala Glu Val Val Lys Pro Gly Ala
            1               5                   10                  15

Ser Val Lys Leu Ser Cys Lys Ala Ser Gly Tyr Thr Phe Thr Thr Phe
                            20                  25                  30

Trp Met His Trp Val Arg Gln Ala Pro Gly Gln Gly Leu Glu Trp Ile
                        35                  40                  45

Gly Asn Ile Tyr Pro Gly Ser Gly Ile Ser Asn Tyr Asp Glu Lys Phe
            50                  55                  60

Lys Asn Arg Ala Thr Leu Thr Val Asp Thr Ser Ile Ser Thr Ala Tyr
            65                  70                  75                  80

Met Glu Val Ser Arg Leu Arg Ser Glu Asp Thr Ala Val Tyr Tyr Cys
                            85                  90                  95

Thr Thr Gly Trp Asp Gly Glu His Trp Gly Gln Gly Thr Thr Leu Thr
                            100                 105                 110

Val Ser Ser Ala Ser Thr Lys Gly Pro Ser Val Phe Pro Leu Ala Pro
                            115                 120                 125

Ser Ser Lys Ser Thr Ser Gly Gly Thr Ala Ala Leu Gly Cys Leu Val
                            130                 135                 140

Lys Asp Tyr Phe Pro Glu Pro Val Thr Val Ser Trp Asn Ser Gly Ala
```

```
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Asp Glu Leu Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
                435                 440                 445

<210> SEQ ID NO 118
<211> LENGTH: 445
<212> TYPE: PRT
<213> ORGANISM: Artificial Sequence
<220> FEATURE:
<223> OTHER INFORMATION: Humanized heavy chains

<400> SEQUENCE: 118

Gln Val Gln Leu Val Gln Ser Gly Ala Glu Val Val Lys Pro Gly Ala
1               5                   10                  15
Ser Val Lys Leu Ser Cys Lys Ala Ser Gly Tyr Thr Phe Thr Thr Phe
                20                  25                  30
Trp Met His Trp Val Lys Gln Ala Pro Gly Gln Gly Leu Glu Trp Ile
                35                  40                  45
Gly Asn Ile Tyr Pro Gly Ser Gly Ile Ser Asn Tyr Asp Glu Lys Phe
                50                  55                  60
Lys Asn Arg Ala Thr Leu Thr Val Asp Thr Ser Ile Ser Thr Ala Tyr
```

```
                65                  70                  75                  80
Met Glu Val Ser Arg Leu Arg Ser Glu Asp Thr Ala Val Tyr Tyr Cys
                    85                  90                  95

Thr Thr Gly Trp Asp Gly Glu His Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```